US00PP15228P2

(12) United States Plant Patent
DeJong et al.

(10) Patent No.: US PP15,228 P2
(45) Date of Patent: Oct. 12, 2004

(54) PEACH AND NECTARINE ROOTSTOCK NAMED 'K146-43'

(50) Latin Name: ***Prunus saliciana*×*P. persica***
Varietal Denomination: cv. K146-43

(75) Inventors: Theodore DeJong, Davis, CA (US); David Ramming, Fresno, CA (US); R. Scott Johnson, Clovis, CA (US); James Doyle, Clovis, CA (US)

(73) Assignees: The Regents of the University of California, Oakland, CA (US); The United States of America as represented by the Secretary of Agriculture, Washington, DC (US)

( * ) Notice: Subject to any disclaimer, the term of this patent is extended or adjusted under 35 U.S.C. 154(b) by 15 days.

(21) Appl. No.: 10/438,487

(22) Filed: May 15, 2003

(51) Int. Cl.[7] ..... A01H 5/00
(52) U.S. Cl. ..... Plt./180
(58) Field of Search ..... Plt./180

(56) References Cited

PUBLICATIONS

Basile, Boris et al. (2003) "Daily shoot extension growth of peach trees growing on rootstocks that reduce scion growth is related to daily dynamics of stem water potential" Tree Physiology 23: 1–10.
DeJong, Ted M. et al. (1991) "Evaluation of Size Controlling Rootstocks for California Peach, Plum and Nectarine Production" CTFA Research Report: 4 pages.
DeJong, Ted M. et al. (1992) "Evaluation of Size Controlling Rootstocks for California Peach, Plum and Nectarine Production" CTFA Research Report: 5 pages.
DeJong, Ted M. et al. (1994) "Evaluation of Size Controlling Rootstocks for California Peach, Plum and Nectarine Production" CTFA Research Report: 3 pages.
DeJong, T.M. et al. (1995) "Evaluation of Size Controlling Rootstocks for California Peach Production" Cling Peach Research Report: 3 pages.
DeJong, T.M. et al. (1999) "Evaluation of Size Controlling Rootstocks for California Peach Production" Cling Peach and CTFA Research Report: 5 pages.
DeJong, T.M. et al. (2000) "Evaluation of Size Controlling Rootstocks for California Peach Production" Cling Peach and CTFA Research Report: 7 pages.
DeJong, T.M. et al. (2001) "Evaluation of Size Controlling Rootstocks for California Peach Production" Cling Peach and CTFA Research Report: 8 pages.
DeJong, T.M. et al. (2002) "Evaluation of Size Controlling Rootstocks for California Peach Production" Cling Peach and CTFA Research Report: 6 pages.
DeJong, T.M. et al. (2001) "Evaluation of Size Controlling Rootstocks for California Peach Production" Proc. 7th Int. Symp. on Orch. & Plant. Syst.: 103–110.
Memorandum of Understanding between the California Tree Fruit Agreement and the Regents of the University of California (2002): 4 pages.
Test Agreement for Rootstocks between Sarb Johl and the Regents of the University of California (2001): 6 pages.

*Primary Examiner*—Kent Bell
*Assistant Examiner*—S. B. McCormick-Ewoldt
(74) *Attorney, Agent, or Firm*—Morrison & Foerster LLP

(57) ABSTRACT

The 'K146-43' rootstock is an inter-specific hybrid rootstock, useful primarily as a commercial understock for peach and nectarine cultivars. The stock has been successfully propagated clonally by hardwood cuttings. This rootstock imparts a substantial degree of vigor control to the scion cultivar that is propagated on top of it. The utilization of adapted growth controlling rootstocks in commercial orchard situations reduces the height of the individual orchard tree without compromising the quality of the fruit. This in turn increases the efficiency of various cultural operations such as pruning, thinning and harvesting by reducing the need for workers in the field to use tall ladders when carrying out these operations.

9 Drawing Sheets

Botanical/commercial classification: Inter-specific hybrid (*Prunus saliciana*×*P. persica*)/Peach and Nectarine Rootstock.
Varietal denomination: cv. K146-43.

BACKGROUND OF THE INVENTION

Field of the Invention

Over half of the annual production costs for California peaches involve hand labor for pruning, thinning and harvesting which is done on ladders because of the large size of the trees. It is widely recognized that production costs could be substantially reduced if the size of the trees could be reduced enough to eliminate the need for ladders in the orchard. The benefit of size controlling rootstocks has been clearly demonstrated in apples and revolutionized the apple industries in Europe and the U.S.

The primary factor in limiting the use of size-controlling rootstocks in stone fruit production is the lack of availability of suitable size controlling rootstocks with a wide range of compatibility among cultivars. In particular, there is a tremendous need for size-controlling rootstocks compatible with peach and nectarine.

SUMMARY OF THE INVENTION

'K146-43' is an inter-specific hybrid (*Prunus saliciana*×*P. persica*) rootstock that is graft compatible with peach and nectarine (*P. persica*) scion cultivars and confers size-control (approx. 40–50%) to the peach scions. 'Flavorcrest' peach, the parent peach trees grown on this rootstock, are productive, smaller and require less pruning than trees grown on standard commercial rootstock ('Nemaguard').

'K146-43' is an inter-specific seedling genotype derived from a cross made in 1979 between *Prunus salicina* ('K47-31' plum, an un-named selection from the USDA, ARS Fresno breeding program) and *Prunus persica* ('Flavorcrest' peach) which is not patented. The seed were stratified germinated in the greenhouse and the seedlings planted in the field in the spring of 1980 at USDA, ARS, Postharvest Quarantine and Genetics Research Unit plots at the University of California research plots at Kearney Agricultural Center, Parlier, Calif. 93648. The plant was subsequently budded in the nursery in 1982 and planted at USDA, ARS, Postharvest Quarantine and Genetics Research Unit in Fresno, Calif. The first propagation trial was done in 1982 from cuttings from the original tree. 'K146-43' was first asexually propagated from hardwood cuttings in Fresno, Calif. and subsequently in Oakdale, Parlier, Davis, and Newcastle, Calif. Only 8.3% of the cuttings grew in this first propagation trial but subsequent propagation trials have resulted in >80% success. New cultivar 'K146-43', in comparison with the parent 'K47-31', is a peach-plum hybrid and so has intermediate characteristics between typical peach and Japanese plum cultivars. 'K146-43' produces no fruit and is suitable as a rootstock only. The parent 'K47-31,' in contrast, is a Japanese plum (*Prunus salicina*) and thus has all the characteristics of typical fruiting Japanese plum varieties. The propagaules obtained through succeeding asexual propagation of 'K146-43' retain the new distinctive characteristics and reproduce true to type, as demonstrated in the statistical data in the Tables. Initial screening of 'K146-43' for susceptibility to rootknot nematode indicated that 'K146-43' is mildly susceptible.

In November, 1986, cuttings of 'K146-43' were made and planted in a commercial nursery, budded in the nursery in May 1987, and planted at the University of California, Kearney Agricultural Center in January 1988. This was a large rootstock evaluation trial involving more that 80 potential peach rootstock genotypes. The peach scion cultivar used in this trial was O'Henry. After 7 years of collecting field data in this trial, 'K146-43' was selected for further replicated field productivity trials based on its ease of propagation from cuttings, lack of root suckering, compatibility with peach scions and major size-controlling characteristics. Crop productivity of the O'Henry scion cultivar grown on 'K146-43' was excellent considering the reduced tree stature.

'K146-43' was propagated again by taking cuttings in November 1994 and planted in a commercial nursery, budded in the nursery in June 1995, and planted at University of California, Kearney Agricultural Center in February 1996. This was a large, replicated field productivity trial involving the eight best potential rootstock genotypes from the 1987 trial. The peach scion cultivars for the main part of this trial were 'Flavorcrest' and 'Loadel'. After eight years of collecting tree performance data, 'K146-43' stands out as a rootstock that has major size-controlling potential (tree size equal to 50–60% of trees on the standard industry rootstock, 'Nemaguard') and would be acceptable for commercial use. Additional field trials in growers' orchards have been initiated and to date these trials corroborate previous findings.

BRIEF DESCRIPTION OF THE DRAWINGS

FIG. 9 shows pictures of peach trees grown at the UC Kearney Agricultural Center, Parlier, Fresno County, Calif.

BOTANICAL DESCRIPTION OF THE PLANT

Figure 1:
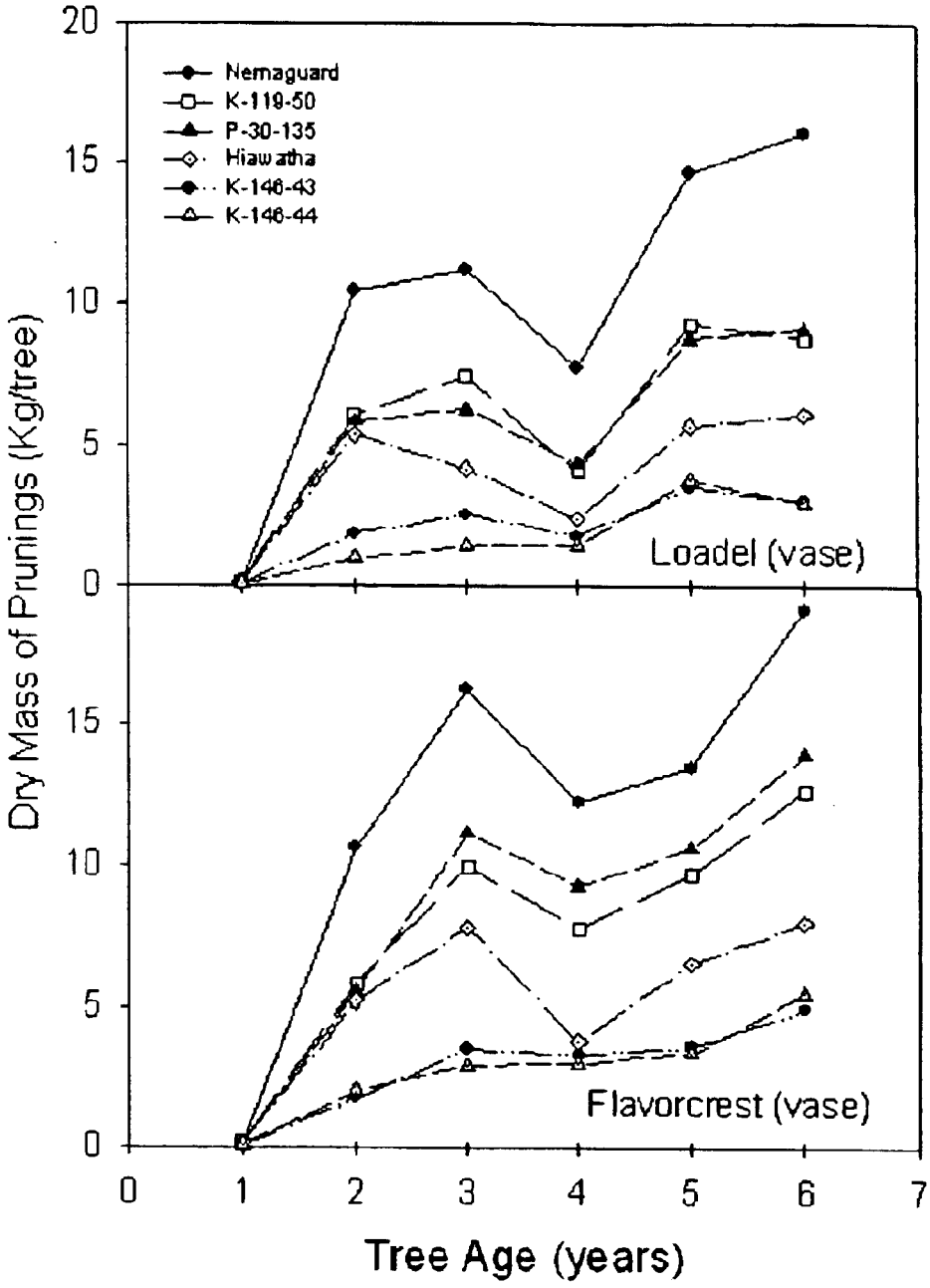
FIG. 1 shows comparisons of pruning weights (summer and dormant season combined) for open vase trained 'Loadel' (Top) and 'Flavorcrest' (Bottom) peach trees on six different rootstocks during the first six years in the orchard.

The following horticultural description was developed from plant material of the new cultivar growing at the University of California Kearney Agricultural Center (KAC) in Parlier, Calif. Trees were observed during the year 2002 growing season when they were approximately ten years old. Color definitions used throughout the following description are from "The Royal Horticultural Society Colour Chart" 3$^{rd}$ edition published in 1995. The new cultivar is an interspecific hybrid, the result of a cross between *Prunus salicina* (cv. USDA Selection 'K47-31') and *Prunus persica* (cv. 'Flavorcrest'). As a result of this pedigree some phenotypic characters of this cultivar resemble the peach parent and others favor the plum parent.

TREE

The trees from which this description has been made were first planted at KAC as a source of cutting material from which to propagate the new rootstock for experimental plantings. Trees of peach rootstock were planted in 1993 and grafted later that same year with wood of 'K146-43'. The propagated trees were grown normally in an open vase training system for two years. Since that time they have received a rather severe annual pruning to keep them in a highly vegetative state. The heavy pruning favors the development of many long straight shoots especially suited for the production of clonal rooted cuttings. The tree of the subject new cultivar is vigorous and hardy under typical San Joaquin Valley climatic conditions. Tree form is upright to upright-spreading. Tree height at the end of the 2002 growing season ranges from 2.6 to 2.9 meters, with 1.65 to 1.78 meters of that height in new, current season's growth in the upper portion of the tree. Lower in the tree, current season's growth ranges from 0.38 to 0.64 meters. Tree width across the crown of the tree ranges from 1.52 meters down the row to 2.13 meters across the row. The trees are located in a high density planting with 3.66 meters between the tree rows and 1.52 meters between each tree.

TRUNK

The lower 28 to 31 cm of the trunk of the subject trees is peach rootstock. The trunk of the 'K146-43' topstock at the point of union with the peach root ranges from 12.5 to 12.8 cm in diameter. The trunk surface is relatively rough and furrowed with a moderate amount of scarfskin present. Trunk color ranges from a very dark brown on the oldest surfaces (Fan#4, Sheet 200-A) to a lighter grey (Fan#4, Sheet 201-A). Growth cracks in the older wood have a lighter color, ranging from a brown-tan (Fan#4, Sheet 165-B) to a darker grey-brown (Fan#4, Sheet 199-A). Bark lenticels on the trunk are moderately numerous but relatively small, ranging from 1.5 to 3.5 mm in width and from 0.5 to 1.5 mm in height. Lenticel color ranges from a light grey (Fan#4, Sheet 201-B) to a grey-brown (Fan#4, Sheet 199-B). Lenticel shape is a broad oval, substantially flattened vertically.

BRANCHES

The tree branches are in the normal range of thickness and appear intermediate in appearance between the peach parent and the plum parent. The primary scaffolds arising from the trunk, range from 5.1 to 6.9 cm in basal diameter. Base diameter of upper spreader limbs ranges from 2.8 to 4.8 cm. Base diameter of lower and smaller hanger wood ranges from 0.8 to 1.5 cm. Older branch surfaces are netted and lightly furrowed with a moderate amount of scarfskin present. Branch surface color ranges from dark brown (Fan#4, Sheet 165-A) to a lighter brown (Fan#4, Sheet 165-B). Numerous small and flattened bark lenticels are present. Lenticel size ranges from 1.0 to 5.0 mm in width and from 0.5 to 1.0 mm in height. Lenticel color on the older branches varies from a grayish-brown (Fan#4, Sheet 199-A) to a lighter brown (Fan#4, Sheet 165-B). Short spurs can arise along two-year-old or older wood. These spurs usually fall within a length range of from 5 to 25 mm. Such spurs usually produce a high number of buds, from 8 to 30, depending on the length of the spur.

Younger, current-season shoots vary in color from a medium yellow-green (Fan#3, Sheet 144-B) to a darker green (Fan#3, Sheet 146-C). These shoots can eventually become partially or fully brown later in the season (Fan#4, Sheet 199-C). The surface of younger shoots is relatively smooth and glabrous, becoming somewhat netted on the surface during the latter part of the season. Bark lenticels on the young wood are numerous, appearing initially as light greenish colored dots only about 0.5 mm in diameter (Fan#3, Sheet 144-C). These lenticels darken throughout the season. Internode length of hanger wood is in the average range, from 15 to 25 mm between the nodes.

LEAVES

The leaves are medium in size. Measurements have been taken from leaves growing near the midpoint of upright vigorous shoots. Leaf length ranges from 12.3 to 15.9 cm, including the petiole. Leaf width ranges from 4.3 to 5.3 cm. Leaf thickness is normal. Leaf surface is moderately rugose.

LEAF FORM

The leaf form is lanceolate. The leaf apices are slightly variable, ranging from acute to at times acuminate.

LEAF COLOR

Color of the upper leaf surface is a dark green (Fan #3, Sheet 146-A to Sheet 146-B). The lower leaf surface is a lighter grey-green in color (Fan #3, Sheet 146-D).

LEAF MARGINS

Leaf margin form is crenate. The individual crenations are medium in size and moderately uniform. The margins are very slightly undulate. At full maturity, leaf margins often roll downwards under the plane of the leaf.

LEAF PETIOLE

The leaf petioles are of average size. The petioles range from 10 to 16 mm in length and from 1.5 to 2.0 mm in thickness. The petiole surface is pubescent, with an abundance of short pubescence. Petiole color is a light green-yellow (Fan #3, Sheet 145-B). No stipules are present in late summer.

LEAF GLANDS

All leaf glands are reniform in shape but vary in position on the leaf. From 0 to 2 glands can be present on the leaf petiole. When present in this position, the glands almost always are present on a stalk. From 2 to 4 glands can be present on the leaf blade margins. These glands are always positioned along the basal portion of the leaf margin and are not on stalks.

FRUIT

The 'K146-43' tree is sterile and does not produce fruit. Most likely the interspecific parentage of this new variety is the cause of its sterility.

FLORAL DESCRIPTION

The following description was developed from floral plant material obtained from trees of 'K146-43' growing at the UC Kearney Agricultural Center, Parlier, Fresno County, Calif. The flowers were described in March of 2002.

[FLOWER BUDS]

SIZE

The flower buds range from small to medium in size. Buds range from 3 to 4 mm in length and from 1.5 to 2.0 mm in width.

FORM

The buds are relatively narrow and pointed. The buds are moderately appressed to the bearing shoot. The buds are hardy under typical San Joaquin Valley climatic conditions.

COLOR

The bud scales are a medium brown (Fan#4, Sheet 200-C).

BUD SURFACE

The surface of the buds is lightly pubescent, with the pubescence most evident along the upper margins of the bud scales.

BLOOM TIMING

The date of bloom is average in relation to standard peach cultivars grown commercially in the San Joaquin Valley. The date of appearance of first bloom was Mar. 3, 2002. Date of full bloom was March 8, 2002.

FLOWER SIZE

The flower of 'K146-43' is of the showy type and is in the medium range of this specific flower type. Flowers in a fully expanded condition, range from 28 to 32 mm in diameter. Many blossoms do not open fully, but remain in a somewhat cupped position even at full maturity.

BLOOM QUANTITY

The quantity of bloom produced is moderate to slightly less than average. Initially 2 to 4 buds are present per node, with 2 to 3 buds most common. Prior to bloom, many buds abscise from the tree.

FLOWER PETALS

The flower petals are generally of medium size. Petal length varies from 16 to 18 mm and petal width from 13 to 17 mm. Petal number is five. The petal form is very broadly ovate. The petal color is generally a very light pink (Fan#2, Sheet 69-C) over most of the petal surface. A darker pink color is present basally and over the petal claw (Fan#2, Sheet 62-C). The petal claw is truncate in form. Claw width ranges from 1.5 to 2.0 mm and claw length averages 1.0 mm. The petal margins are moderately undulate and strongly cupped inwards. The petal apices are variable from generally rounded to notched.

FLOWER PEDICEL

The flower pedicel is very short. Pedicel length ranges from 1.0 to 1.5 mm. Pedicel thickness ranges from 1.0 to 1.5 mm. Color of the pedicel is a bright shiny green (Fan#3, Sheet 144-C). The pedicel surface is glabrous.

FLORAL NECTARIES

The floral nectary color is a greenish-yellow (Fan#3, Sheet 151-B).

CALYX

The calyx surface is glabrous and very rugose. The underlying color of the calyx and calyx veins is greenish (Fan#3, Sheet 144-C). Purple speckling is present on the calyx interveinal areas (Fan#2, Sheet 63-A).

SEPALS

Sepal surfaces are generally glabrous except along the sepal margins where a moderate amount of pubescence occurs. The sepals are moderately large, ranging from 4 to 5 mm in length and from 4.0 to 4.5 mm in width. Sepal form is broadly ovate. Exterior color of the sepals is primarily dark purple (Fan#2, Sheet 59-C) with occasional areas where the greenish underlying color shows through the purple (Fan#3, Sheet 144-C).

ANTHERS AND POLLEN

The anthers are of average size. Anther color both ventrally and dorsally is a yellow-orange (Fan#1, Sheet 13-A). Pollen is moderately abundant. Pollen color is yellow-orange (Fan#1, Sheet 13-B).

STAMENS

Stamen length is quite variable, from 6 to 11 mm in length. The stamens are much longer when compared to the poorly developed pistil. Stamen color is a very light pink (Fan#4, Sheet 56-D). Stamens become somewhat darker with age.

PISTIL

Pistil length is variable, ranging from 2 to 5 mm including the ovary. Pistil color is a very light yellow-green (Fan#3, Sheet 150-D). The pistil surface is glabrous. The pistil appears thin and essentially undeveloped, probably due to the interspecific parentage of the subject new cultivar.

COMPARISONS

Comparison #1

In February, 1996 a field rootstock trial was established at the University of California Kearney Agricultural Center, Parlier, Calif. The research block consisted of two peach scion cultivars (*Prunus persica* L. Batsch cvs. 'Loadel' (clingstone) and 'Flavorcrest' (freestone) bud-grafted onto ten different rootstock genotypes. The ten rootstocks were 'Alace', 'Hiawatha', 'Sapalta' (open pollinated seedlings of Sapa, a *Prunus besseyi*×*P. salicina* hybrid), 'K-145-5', 'K-146-43', 'K-146-44', 'P-30-135' (*P. salicina*×*P. persica* hybrids) 'K-119-50' (*P. salicina*×*P. dulcis* hybrid) and two control rootstocks, 'Citation' (*P. salicina*×*P. persica*) and 'Nemaguard' (*P. persica*). A total of thirty-six trees of each rootstock/scion combination were planted in two different training systems. Four replications of five trees each were planted and trained to the 'KAC-V' perpendicular V system; (DeJong et. al. 1994) and four replications of four trees each were planted and trained to the standard open vase system (Micke et. al. 1980). Between-row spacing was the same for all rootstock/scion/training system combinations (4.88 m.) but in-row spacing varied according to expectations of final tree size. In-row tree spacing was 1.98 m (1035 trees/ha) for trees on 'Nemaguard' and 'P-30-135' and 1.83 m (1120 trees/ha) for 'K-119-50', 'Alace', 'Hiawatha', 'Sapalta', 'K-145-5', 'K-146-43' and 'K-146-44' in the 'KAC-V' system; and 4.88 m (420 trees/ha) for 'Nemaguard' and 'P-30-135', 4.27 m (480 trees/ha) for 'K-119-50', 'Alace', 'Hiawatha', 'Sapalta' and 'K-145-5', and 3.66 m (560 trees/ha) for 'K-146-43' and 'K-146-44' in the open vase systems. Replication of the rootstock/scion combinations were randomized within training system/scion cultivar subplots. In-row tree spacing between replications in the open vase system was the shortest tree distance within the replications plus one-half the spacing difference between the replications (ie. when a 'Nemaguard' replication was planted adjacent to a 'K-146-43' replication, the in-row spacing between replicates was 4.27 m).

The soil at the site is a well-drained Handford, fine sandy loam. The trees were flood-irrigated to maintain 100% of potential evapo-transpiration prior to harvest and about 80% after harvest. Fertilizer and pesticides were applied according to standard horticultural practices. Weeds were controlled by mowing the row middles and applying herbicides to maintain a 1.5 wide weed-free strip down the tree rows.

Trees were pruned during midsummer and during the dormant season according to standard recommendations for growing the two systems for each year except for years one and four when they were only dormant pruned (DeJong et al. 1999). Severity of pruning was adjusted according to the growth characteristics of each rootstock/scion combination to optimize crop production while developing/maintaining the desired tree shape. The first significant fruit set occurred in the third leaf and crop load was adjusted for tree size by hand thinning to maintain a minimum spacing between fruit. Because patterns of fruit maturity varied somewhat with rootstock, fruit were harvested in several picks but data were combined from all harvests to calculate mean fruit yield. Data on crop load (fruit per tree and fruit size were also recorded but are not reported in this paper).

Results From Comparison #1

Rootstock related differences in tree size and vigor were apparent after the first year of growth in the field. 'Nemaguard' was clearly the most vigorous; followed by 'K-119-50', 'P-30-135', 'Hiawatha', 'K-145-5', 'K-146-43', 'Alace', 'Sapalta', 'K-146-44' and 'Citation', respectively. However, in the fall of the first year in the field several trees of 'Citation', 'K-145-5', 'Alace' and 'Sapalta' appeared unhealthy with premature leaf fall and leaf "boating" and "bronzing". During the subsequent spring several of these trees died while others appeared to recover. But by the following fall, additional trees appeared unhealthy and more died. As a consequence these scion/rootstock combinations were eliminated from the formal experiment and no further data on them was collected. Thus, the remainder of this specification will only report on data from the remaining six rootstocks in the trial ('Nemaguard', 'K-119-50', 'P-30-135', 'Hiawatha', 'K-146-43', 'K-146-44').

After six years in the orchard, overall tree size as indicated by trunk circumference was consistently reduced across all scion/training system combinations by each size-controlling rootstock. (Table 1). Trees on the two most size-controlling rootstocks ('K-146-43' and 'K-146-44') had trunk circumferences that were 61–72% of trees on 'Nemaguard' whereas trees on the least dwarfing rootstock ('P-30-135') had trunk circumferences that were 92–95% of those on 'Nemaguard'. Trees on 'Hiawatha' were 76–87% of those on 'Nemaguard', while trees on 'K-119-50' were 83%–86% of trees on 'Nemaguard'.

Figure 2:
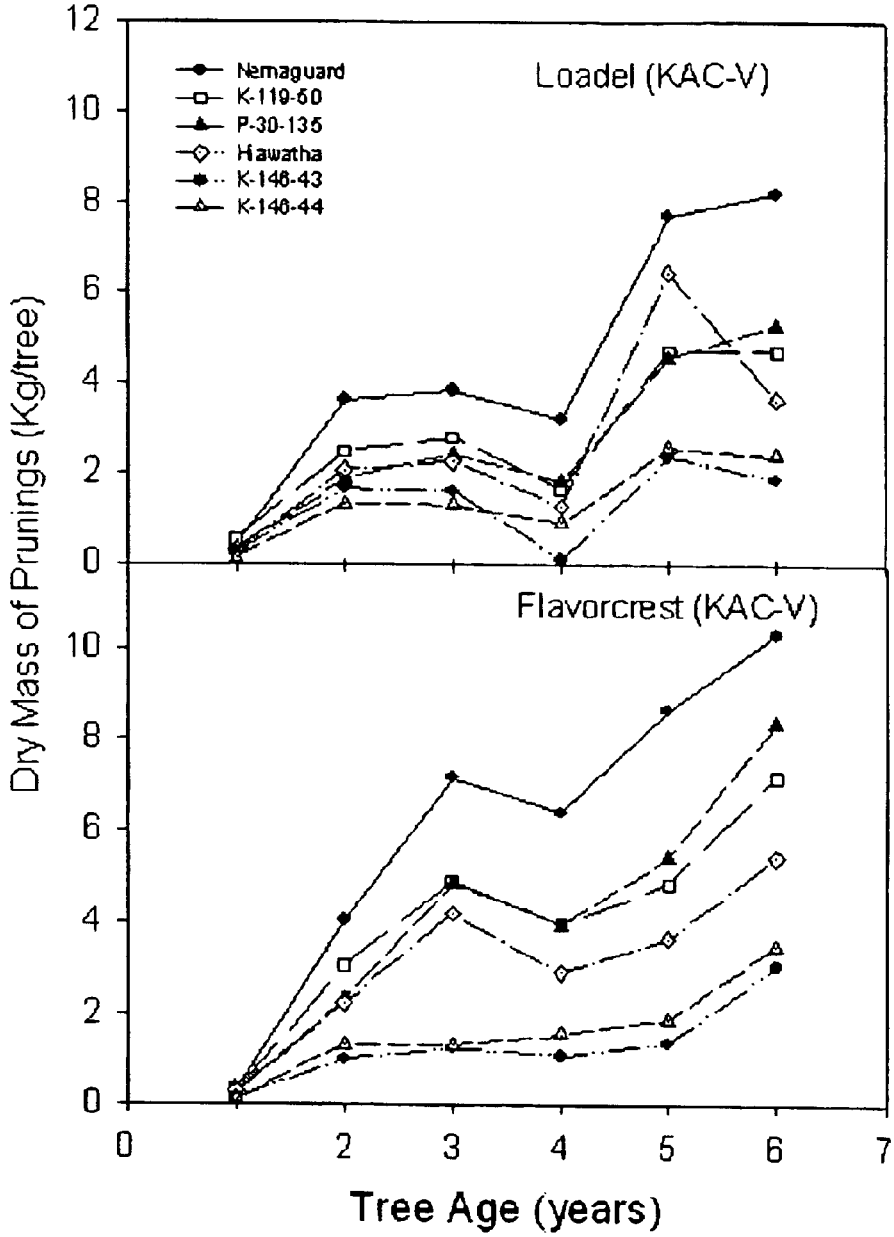
FIG. 2 shows comparisons of pruning weights (summer and dormant season combined) for 'KAC-V' trained, 'Loadel' (Top) and 'Flavorcrest' (Bottom) peach trees on six different rootstocks during the first six years in the orchard.

In spite of the differences in tree size and vigor, all trees were pruned in a manner that was deemed appropriate to maintain optimum fruiting potential for each scion/rootstock/training system combination. Although there were yearly variations in the amount of brush pruned from each combination over the first six years of the trial, a clear picture of the effectiveness of each rootstock on reducing excessive vegetative growth compared to trees on 'Nemaguard' was apparent when the annual pruning weights were plotted for each rootstock/scion/training system combination over the six years of the trial (FIGS. 1 and 2). The effectiveness of the size-controlling rootstocks for reducing the amount of dry matter that needed to be removed during pruning relative to trees on the vigorous control ('Nemaguard') was greater in the larger open vase trees than the higher density 'KAC-V' system. Similarly, the effect of the size-controlling rootstocks on reductions of pruning weights were greater with the more vigorous scion cultivar ('Flavorcrest', an early fresh marker peach) compared to the weaker scion cultivar ('Loadel', an early processing clingstone peach). Perhaps the most interesting aspect of these data are the relatively large reductions in cumulative pruning weights with the size controlling rootstocks over the six years of the trial compared to the more modest differences in trunk circumference which is also a cumulative measurements. For example, the cumulative pruning weights for trees on 'K-146-44' over six years were 17, 23, 32 and 26% of trees on 'Nemaguard' for the 'Loadel'/'KAC-V', 'Flavorcrest'/'KAC-V', 'Loadel'/'Vase', 'Flavorcrest'/'Vase', respectively, while differences in trunk circumferences ranged from 61–72% of trees on 'Nemaguard'. Similarly, cumulative pruning weights for trees on 'P-30-135' ranged from 57–70% of trees on 'Nemaguard' while trunk circumferences on the same rootstock ranged from 92–95% on trees on 'Nemaguard'.

Figure 3:
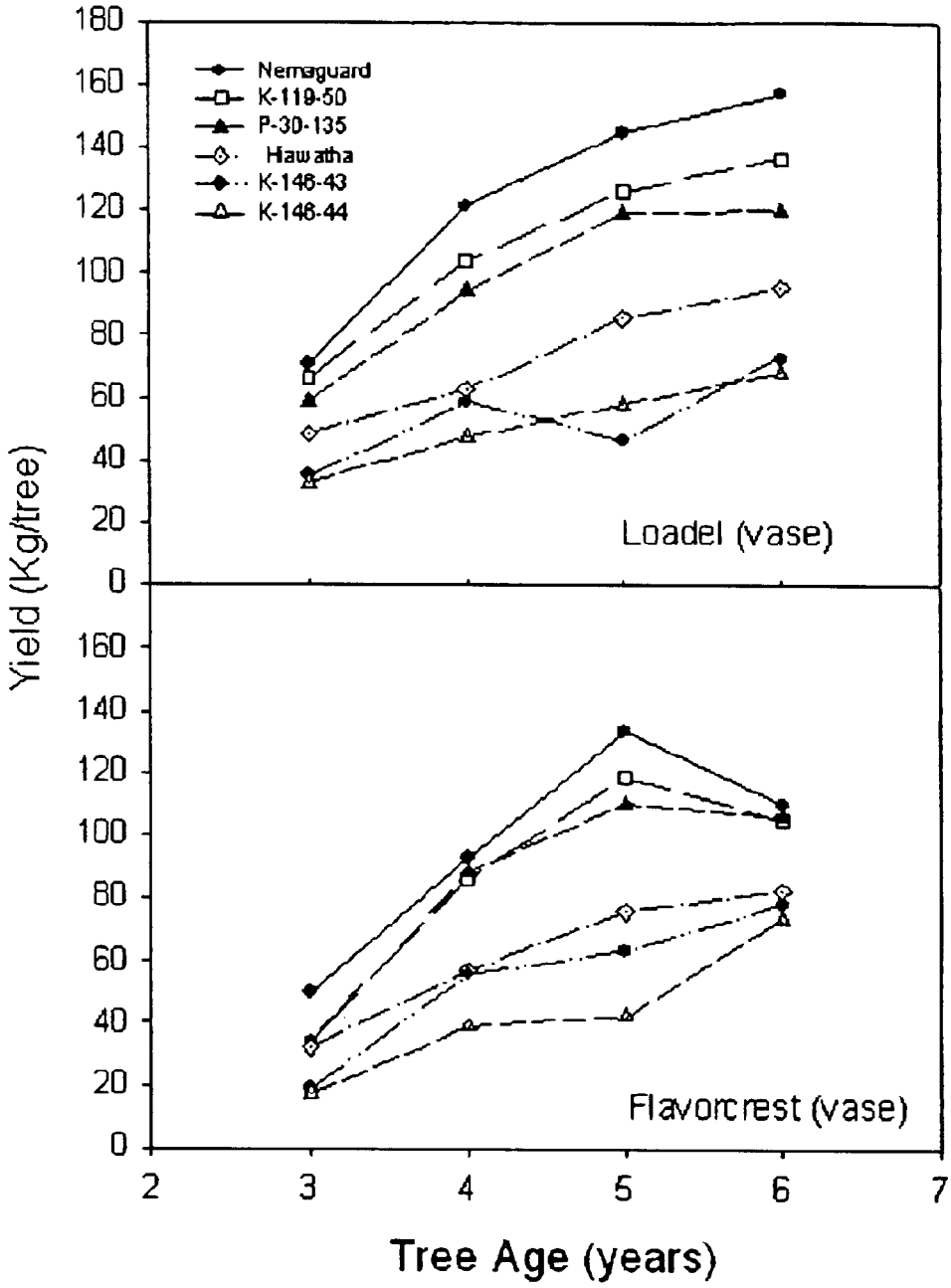
FIG. 3 shows fruit yields (fresh weight) of open vase trained 'Loadel' (Top) and 'Flavorcrest' (Bottom) peach trees on six different rootstocks in years three through six in the orchard.
Figure 4:
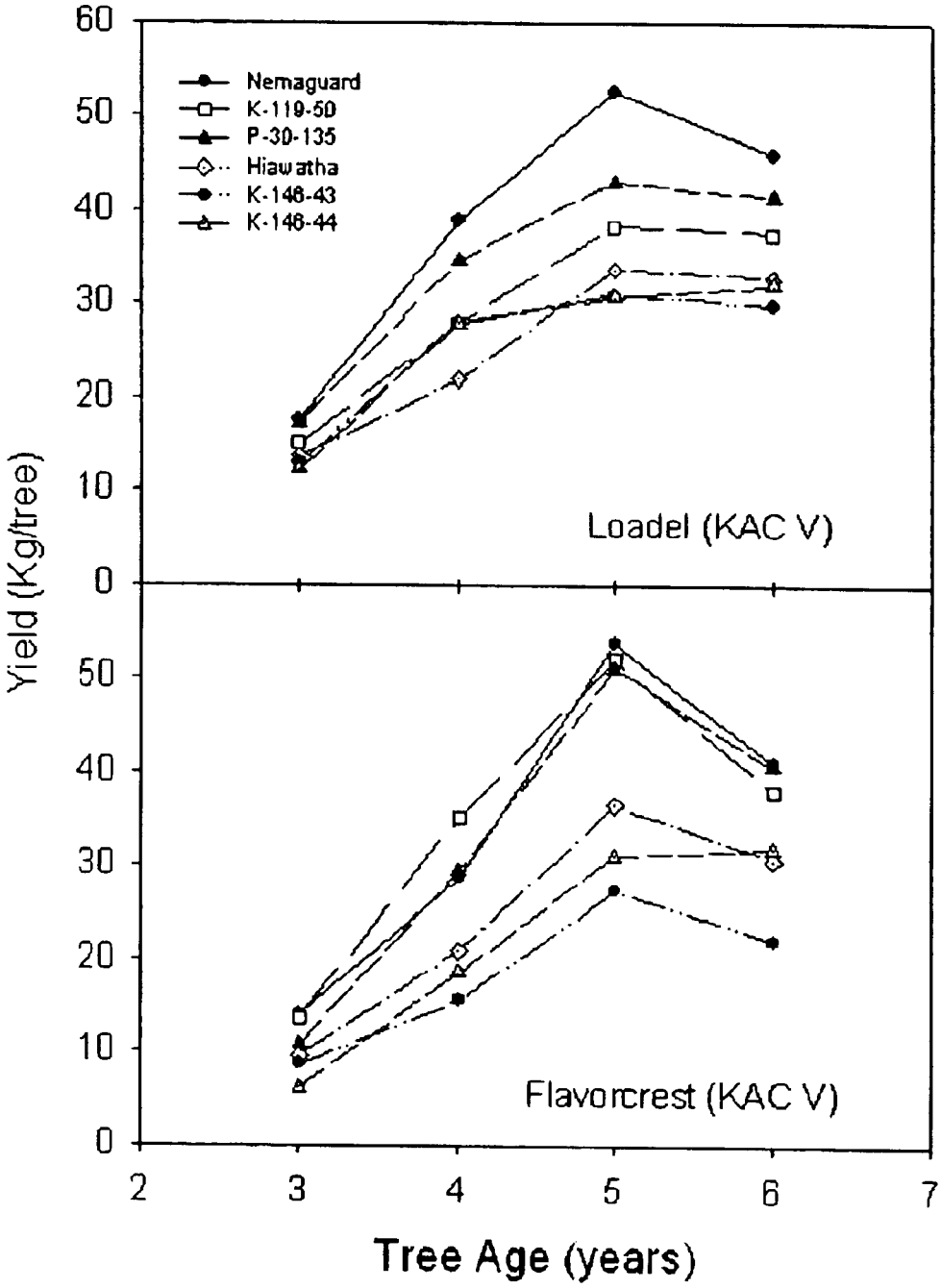
FIG. 4 shows fruit yields (fresh weight) of 'KAC-V' trained 'Loadel' (Top) and 'Flavorcrest' (Bottom) peach trees on six different rootstocks in years three through six in the orchard.

Patterns of crop yield per tree during years three through six in the orchard followed patterns of relative tree size in each scion/rootstock/training system combination (FIGS. 3 and 4). Trees on the more size controlling rootstocks appeared to reach full yield potential at about the same time as trees on the more vigorous rootstocks in the higher density 'KAC-V' system but clearly lagged behind the vigorous rootstocks in the open vase systems so it is difficult to make clear judgements about the final relative yield potentials of the various rootstock/scion combinations in each system other than to note that annual as well as cumulative crop yields per tree are at least 30% lower with the most size-controlling rootstocks compared to trees on 'Nemaguard'. Crop yields of 'Flavorcrest' peaches on 'K-119-50' and 'P-30-135' tended to be more comparable to those on 'Nemaguard' than for 'Loadel' peaches with the same rootstocks. Although no fruit size data are presented here, mean fruit sizes among the three most vigorous cultivars were very similar but the three more size controlling cultivars tended to have somewhat smaller mean fruit sizes. At this time, it is not clear if the fruit size tendencies are a real function of the rootstock or a result of a tendency for the fruit thinners to leave more fruit on the smaller trees relative to the size of the trees.

In an effort to develop information concerning the relative efficiency of each scion/rootstock/training system combination, we converted fruit fresh weight to dry weight and calculated a modified harvest increment (kg annual fruit dry weight/kg annual pruning weight) for each scion/rootstock/training system combination for the four years that we had harvest data (Table 2). Although there was substantial variation between years, all of the experimental rootstocks had higher mean modified harvest increments than trees on 'Nemaguard' for a given year within each scion/training system combination. Also there was a general tendency for trees in the open vase system to have higher modified harvest increments than trees in the 'KAC-V' system. Similarly, the less vigorous, more heavily cropped 'Loadel' trees tended to have higher values than the 'Flavorcrest' trees for each rootstock/training system combination. The high amount of variability in these data was due to variability in pruning and fruit thinning practices as well as the biological variability inherent in the scion/rootstock/training systems combinations. However, the general trends in the data clearly indicate the size-controlling rootstocks have the potential to increase partitioning of dry matter to fruit, relative to vegetative growth, for a given scion/training system combination. Thus, if training systems and tree densities can be feasibly adjusted so that total annual accumulation of dry matter in an orchard is comparable to what is currently achieved with trees on 'Nemaguard' in California, it should be possible to increase crop yields with smaller trees using these size-controlling rootstocks. Intensive studies of growth characteristics of the trees on various rootstocks indicate that the primary differences between the scions on the size controlling rootstocks and trees on 'Nemaguard' are related to shoot internode length and shoot extension growth rate (Weibel et al., 2002). Furthermore, these factors appear to be related to differences in diurnal patterns of stem water potential (Basile et al., 2002a) and root hydraulic conductance (Basile et al., 2002b).

LITERATURE CITED FOR COMPARISON #1

Basile, B., J. Marsal and T. M. DeJong. 2002a Daily shoot extension growth of peach trees growing on rootstocks that reduce scion growth is related to daily dynamics of stem water potential. (in press)

Basile, B., J. Marsal, L. I. Solari, M. T. Tyree, D. R. Bryla and T. M. DeJong. 2002b. Hydraulic conductance of peach trees grafted on rootstocks with differing size-controlling potentials. (in press)

DeJong, T. M., K. R. Day, J. F. Doyle and R. S. Johnson. 1994. The Kearney Agricultural Center Perpendicular "V" (KAC-C) orchard system for peaches and nectarines. HortTech. 4:362–367.

DeJong, T. M., W. Tsuji, H. F. Doyle and Y. L. Grossman. 1999. Comparative economic efficiency of four peach production systems in California. HortScience 34(1):73–78.

Micke, W., A. A. Hewitt, J. K. Clark and M. Gerdts. 1980. Pruning Fruit and Nut Trees. University of California Div. of Agric. Sci. Leaflet 21171.

Rom, R. C. and R. F. Carlson. 1987. Rootstocks for fruit crops. Wiley Press, New York. 494p.

Weibel, A, R. S. Johnson and T. M. DeJong. 2002. Comparative vegetative growth responses of two peach cultivars grown on size-controlling vs standard rootstocks. (in press)

Comparison #2

Data were obtained in 1998 and 1999 on two peach [*Prunus persica* (L.) Batsch] cultivars, 'Flavorcrest' (an early fresh market, freestone cultivar) and 'Loadel' (an early clingstone, processing cultivar) grafted on six different rootstocks: 'Nemaguard' (*P. persica* seedling, the standard vigorous rootstock for California), 'Hiawatha' (open-pollinated seedling of a *P. besseyi* Bailey×*P. salicina* Lindl. hybrid), 'K-146-43', 'K-146-44', 'P-30-135' [*P. salicina* Lindl.×*P. persica* (L.) Batsch hybrids] and 'K-119-50' [*P. salicina* Lindl.×*P. dulcis* (Mill.) D. A. Webb hybrid]. Trees were planted at Kearney Agricultural Center of the University of California, Parlier, Calif. in 1996. Trees were trained to the standard open vase system and spaced in relation to the anticipated size of rootstock/scion combination. Densities were 420, 480 and 560 trees/ha for 'Nemaguard' and 'P-30-135', 'K-119-50' and 'Hiawatha', and 'K-146-44' and 'K-146-43' trees, respectively. Trees were planted in a randomized complete block design with four replications and four trees per replicate. The plot was managed according to normal commercial practices with a herbicide strip in the tree row and a mowed cover crop strip between rows. Trees were flood irrigated to replace 100% of estimated evapotranspiration. Seasonal temperature was recorded at a CIMIS (California Irrigation Management Information System) station located within 1 km of the plot. Vegetative growth was monitored by measuring trunk cross-sectional area (TCA), shoot and internode length, summer and winter pruning weights, and diurnal extension growth.

Trunk cross-sectional area, shoot and internode growth. Initial and final trunk diameters at 20 cm from the soil were measured on all treatment trees at the beginning and after the end of the 1998 growing season. Trunk cross-sectional area (TCA) was subsequently calculated assuming a circular trunk. Seasonal increment in TCA was followed on one tree per treatment replicate (the tree closest to the mean size) at intervals of 20–30 days during the growing season. Daily growth rate and percent of total annual TCA increment were calculated to compare the cycle of trunk growth among different rootstocks.

Shoot length growth during the season was measured on two scaffolds in the same trees of each rootstock replicate that were selected for measurement of seasonal growth of the TCA in both varieties. Three different types of shoots were selected and tagged: shoots arising directly from the scaffold (S), shoots arising near the base of previous year hanger shoots (B) and terminal shoots growing from the same hangers (T). Hangers are defined as unbranched one-year old shoots from the previous season that were selected for fruit bearing during dormant pruning. Shoot growth was recorded every 20–30 days from May to October.

In January 1999, the number of nodes were counted on each of the tagged shoots in the 'Loadel' trees. Mean length of each type of shoot from the two scaffolds was also measured. Mean internode length was calculated for trees on each rootstock based on node number and shoot length data. One medium-sized scaffold was tagged from each of the selected trees, and the number and length of one-year old shoots, new lateral shoots and watersprout shoots were recorded. Angles of insertion of shoots that came directly from the scaffold were also measured. All scaffold diameters of these trees were also measured at the base of the scaffolds at the beginning and the end of the growing season in 1998 to establish the yearly increase of the scaffold cross-sectional area (SCA). The number of shoots and laterals per tree were calculated for each rootstock based on data from the one scaffold and its SCA compared to the total SCA of the whole tree. The length of primary growth originating from dormant buds from the previous season was calculated for each tree. Secondary and tertiary growth generated from buds formed during the current season was also estimated. By adding these three kinds of growth, the total shoot growth was calculated per tree considering the total primary, secondary and tertiary shoot length growth per measured scaffold and the total SCA of the tree. Shoot growth data from the measured scaffold was multiplied by the ratio: total SCA/individual SCA. Additionally, the ratio between the different measured parameters and the increment in the scaffold cross-sectional area (SCA) was calculated.

The current-year shoots with lateral shoots and basal diameters more than 7.5 mm were considered to be watersprouts and their diameters, number of laterals, primary, secondary, tertiary and total length growth were recorded separately. Number of watersprouts and laterals, and length of watersprout growth per tree were calculated by the same procedure used for shoots. Relationships between shoot length and increase of SCA were compared among rootstocks.

Diurnal stem extension growth rate. Diurnal stem extension rate (SER) was measured on well exposed vigorous shoots on 'Loadel' open vase trees. SER was measured by making fine ink marks with a permanent marker on selected stems on Jun. 22–23, 1999. The distance between fine marks was measured at approximately 4-h intervals during the day and 6-h intervals in the night with a digital caliper. SER was determined by dividing the length increment (amount of change in distance between marks) by the amount of time between measurements (Berman and DeJong, 1997b). SER was studied on two kind of shoots: Terminal shoots on hangers at ~1.5 m from the soil surface and vigorous upright watersprouts in the upper part (~3 m) of the trees. The largest shoots (watersprouts) in each of the trees per replicate (two trees per replication) were used. For the terminal shoots, one growing shoot per tree and replicate was selected. Stem water potential ($\Psi_{ST}$) was measured on mature leaves, close to the scaffolds. Leaves were covered with aluminum covered plastic bags (McCutchan and Shackel, 1992) at least one hour before the measurements. After this period, it was assumed the leaf $\Psi_W$ was equilibrated with that of the xylem sap to which the leaf was attached. Then, the leaves were cut and put in the pressure chamber (model 3005, Soil Moisture Equipment Corporation, Santa Barbara, Calif. Two leaves per tree were used to measure stem water potential.

Influence of rootstocks on pruning weights. All trees except the ones chosen for the previously described seasonal shoot growth measurements were summer pruned on Aug. 18, 1998. Summer pruning consisted of removing only water sprouts and competitive, vigorous shoots on the main scaffolds. Fresh weight of the harvested material was obtained from individual trees. Stems and leaves from one tree per block were dried at 65° C. to convert fresh weight to dry weight. All trees were also dormant pruned in January 1999. Samples of fresh weight from each rootstock/scion combination were dried at 65° C. to convert fresh weight to dry weight. Dormant pruning consisted of removing vigorous shoots and shaded limbs. Strong, upright fruiting shoots were headed and the remaining shoots were thinned as required for the next season's fruit production.

Fruit yield measurements. Standard yield studies were done on 'Loadel' and 'Flavorcrest' trees on the various rootstocks. All trees were normally (commercially) thinned. Fruits were harvested following standard commercial procedures. In 'Loadel' trees, harvest was done in five picks (Jul. 6, 10, 15, 21 and 28, 1998) while 'Flavorcrest' was harvested in three parts (Jun. 19, 23 and 30, 1998). Number of fruits per tree and total fruit weight per tree were recorded. Means were compared using Tukey test (P=0.05).

SAS software (SAS Institute, Cary, N.C.) was used for analyses of variance to test for differences among treatments. Multiple mean separations were carried out using Tukey's multiple range tests (P<0.05).

RESULTS FROM COMPARISON #2

Figure 5:
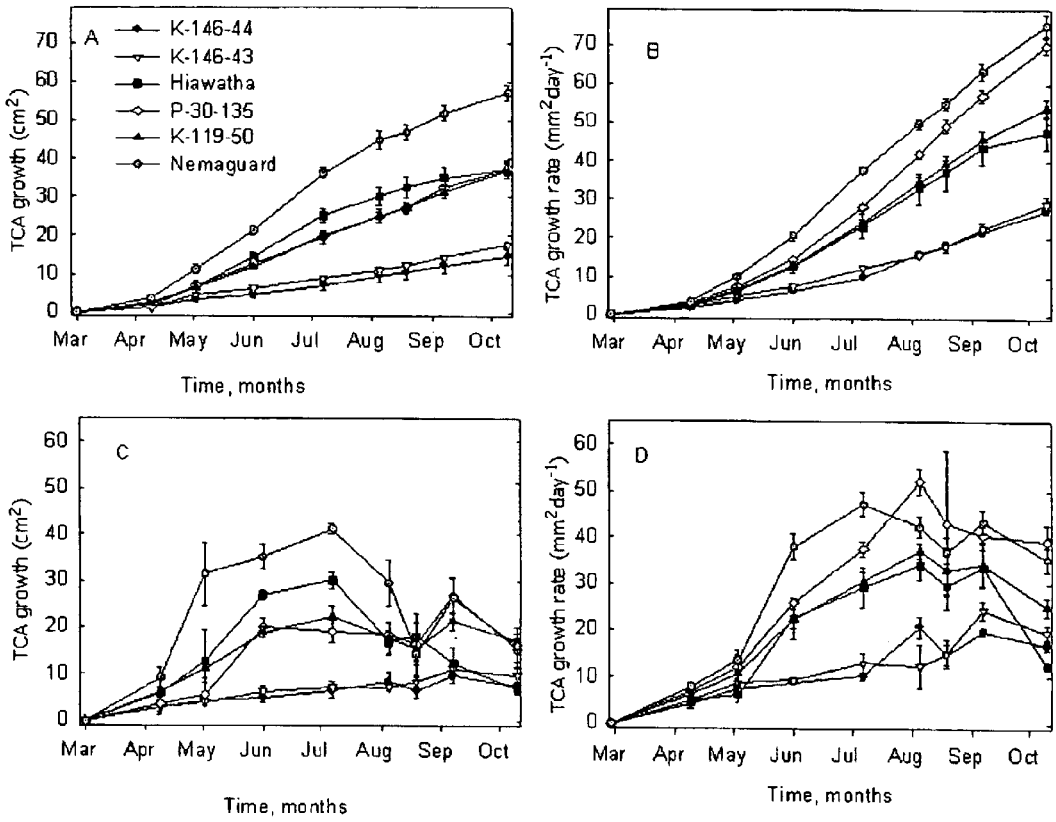
FIG. 5 shows the seasonal pattern of Trunk Cross Sectional Area (TCA) growth of 'Loadel' (A) and 'Flavorcrest' (B) and of TCA growth rate of 'Loadel' (C) and 'Flavorcrest' (D) third leaf open vase peach trees growing on six different rootstocks. Error bars represent ±1 standard error of the mean.

Trunk cross-sectional area (TCA) measurements. The initial TCA and yearly increment were comparable in 'Loadel' and 'Flavorcrest' trees. Trees on 'K-146-44' and 'K-146-43' had the smallest increment in TCA, while trees on 'Nemaguard' had the largest increase with both cultivars (Table 3). During the growing season, 'K-146-44' and 'K-146-43' had a clear negative effect on the TCA growth rate relative to the other rootstocks (FIG. 5). Trees on 'Nemaguard' had the largest relative increase of TCA. Trees on 'Nemaguard', the most vigorous rootstock, had the highest percentage increase in TCA during the first and middle part of season. Trees grafted on 'P-30-135' and 'K-119-50' grew at an intermediate rate during the whole vegetative growing period (FIG. 5).

Seasonal shoot growth pattern. In general, basal shoots (B) on one-year-old fruiting shoots (hangers) reached close to their final length early in the season but 'Loadel' shoots of 'Nemaguard' kept growing later into the season compared to the other rootstocks (FIG. 6A). Shoots on 'Loadel' trees on 'K-146-44' grew early, slowed down and then resumed growth toward the end of the season (FIG. 6A). Shoots on 'Flavorcrest' trees on 'Hiawatha' grew later in the season than the rest of the rootstocks. Shoots on trees grafted on the two most dwarfing rootstocks, 'K-146-44' and 'K-146-43' grew mostly at the beginning of the season (FIG. 6B).

New shoots arising directly from the scaffold branches (S) in 'Loadel' trees on 'Nemaguard' grew more rapidly than the other rootstocks, especially at the beginning of the vegetative season (FIG. 6C). 'Nemaguard' stimulated 'Flavorcrest' S shoot growth more than 'Loadel'. 'Flavorcrest' trees on 'K-146-44' and 'K146-43' had significantly reduced S shoot stem length relative to 'Nemaguard' (FIG. 6D).

Terminal shoots on fruiting hangers growing from terminal buds (T) on 'Loadel' and 'Flavorcrest' trees continued growing almost to the end of the vegetative period. On 'Nemaguard', the 'Loadel' shoots initially grew rapidly and this initial growth was related to the final length. The most size controlling rootstocks, 'K-146-44' and 'K-146-43', produced trees with the shortest shoots during the vegetative period and consequently at the end of the year (FIG. 6E). No statistically significant differences were found among rootstocks for growth of T shoots with 'Flavorcrest', although the measurement means had the same general seasonal pattern as 'Loadel' (FIG. 6F).

Diurnal stem extension growth. On Jun. 22–23, 1999, diurnal growth was measured on two kinds of shoots; terminal shoots and watersprouts. Growth of terminal shoots did not statistically differ, however the mean general trend of terminal shoot growth of trees on 'Nemaguard' was slightly higher than trees on 'K-146-43', especially at midday and early afternoon (FIG. 7B). Stem water potential of trees on 'Nemaguard' was generally less negative than trees on 'K-146-43' (FIG. 7C). Diurnal watersprout shoot growth followed a similar trend as terminal shoots although the absolute growth values of watersprouts were higher (FIG. 7B). Trees on 'K-146-43' tended to have the least growth during the period when stem water potential was recovering and temperature was decreasing. (FIG. 7C).

Shoot growth per tree. 'Loadel' trees on 'Nemaguard' had the highest number of one-year-old shoots per tree and were statistically different from 'K-146-44', which had the lowest number of shoots per tree. Trees on 'Nemaguard' and 'K-119-50' had the most laterals per tree, while trees on 'K-146-44' and 'K-146-43' had approximately one-sixth the number of laterals per tree compared to 'Nemaguard' (Table 4). Trees grafted on 'Nemaguard' produced about three times more primary growth per tree than trees on the most dwarfing rootstock, 'K-146-44'. Growth generated by lateral shoots (secondary and tertiary growth) showed clear differences among rootstocks. Secondary and tertiary growth in trees on 'K-146-44' was less than one-sixth of trees on 'Nemaguard' (Table 4). Total length growth (primary, secondary and tertiary growth) per tree was markedly influenced by rootstocks and followed the same pattern as TCA increment. Growth on 'Nemaguard' was substantially greater than on all the other rootstocks while growth on 'K-146-44' and 'K-146-43' was the least. The amount of one-year-old wood in trees on 'K-146-44' and 'K-146-43' was about one-third that of trees on 'Nemaguard' (Table 4). Between 4.6% and 6.6% of the total estimated numbers of shoots per tree (Table 4) were watersprouts with a basal diameter >7.5 mm. There was a clear trend toward increasing water sprout growth per tree with the more vigorous rootstocks (FIG. 8A) but when expressed on a scaffold cross-sectional area basis, only the smallest rootstocks appeared to differ from 'Nemaguard' (FIG. 8B). On a shoot length basis, watersprout growth of trees on 'P-30-135', 'K-119-50', 'Hiawatha' and 'Nemaguard' represented 48%–53% of the total annual extension growth. In contrast, watersprout growth only represented 26%–32% of the total extension growth per tree for trees on 'K-146-44' and 'K-146-43'.

Insertion angle of shoots arising from scaffolds. The angle between the insertion of one-year-old shoots and scaffolds from which they originated appeared not to be influenced by the rootstocks. Similar values for all the rootstocks were recorded at the end of the season. The mean angle of insertion varied between 50.4 and 54.9° relative to the scaffold across trees on the various rootstocks.

Number of nodes and internode length of one-year old shoots. Shoots were measured at the end of the season to determine shoot and internode length in 'Loadel'. The mean internode length of the shortest tagged shoots (basal shoots from hangers, B), differed among rootstock (Table 5). Although mean internode lengths only differed significantly between 'Nemaguard' (the longest) and 'Hiawatha' (the shortest), the general pattern among all branch types indicated that internode length was the longest on shoots that grew on trees grafted on 'Nemaguard'. The number of nodes was similar in the different rootstocks, so most of the variation in shoot length was attributable to internode length (Table 5). In the shoots from scaffolds (S), mean internode lengths were largest on trees on 'Nemaguard' and 'K-119-50', and they were statistically different from trees on 'K-146-44' and 'K-146-43'. Trees on 'P-30-135' and 'Hiawatha' had intermediate internode lengths. Trees grafted on 'Nemaguard' and 'K-119-50' had the longest shoots, however there were no significant differences in the number of nodes among trees on the different rootstocks, so again most of the variation was due to mean internode length (Table 3). The longest shoots, T shoots, had the shortest mean internode lengths on trees on 'K-146-44' and 'K-146-43'. Trees on 'Nemaguard' produced the longest T shoots and the differences in length were primarily related to differences in internode length rater than number of nodes. (Table 5).

Pruning weights. In 'Loadel' trees, dry and fresh weight per tree of leaves and stems from summer pruning was highest in trees on 'Nemaguard', followed by trees on 'K-119-50' and 'P-30-135'. Trees on 'K-146-44' and K-146-43 needed just a light pruning (Table 6). With 'Flavorcrest', rootstocks could be separated into three groups on the basis of dry and fresh weight obtained from the summer pruning in August. The greatest vegetative material was taken from trees on 'Nemaguard', and the least from 'K-146-44' and 'K-146-43' trees. Trees on 'K-119-50', 'P-30-135' and 'Hiawatha' were intermediate (Table 6).

Rootstocks also markedly influenced fresh and dry mass removed during dormant pruning. 'Loadel' trees required less dormant pruning than 'Flavorcrest' trees. Fresh and dry weights of prunings per tree were greatest for trees on 'Nemaguard' and the least for 'K-146-44'. Prunings from trees on 'P-30-135' and 'K-119-50' had greater dry and fresh weights than prunings from trees on 'Hiawatha', 'K-146-44' and 'K-146-43' (Table 6). 'Flavorcrest' trees on 'Nemaguard' required significantly more pruning than the other rootstocks. In contrast, trees on 'K-146-44' and 'K-146-43' had the least dormant prunings. (Table 6).

Crop yields. 'Loadel' trees on 'Nemaguard' rootstocks had the largest mean fresh fruit yield per tree. Similarly, 'Flavorcrest' trees on 'Nemaguard' also had greater yield per tree than trees on all the other rootstocks but less than the 'Loadel' trees (Table 7). The differences in crop yield between trees on the various rootstocks corresponded fairly well to differences in tree size with both the 'Loadel' and 'Flavorcrest' trees on the two most size-controlling rootstocks ('K-146-43' and 'K-146-44') carrying the least numbers of fruit and producing the lowest yields (Table 7). The mean fruit size on the smaller rootstocks also tended to be less than for trees on the more vigorous rootstocks (data not shown).

Figure 9A:
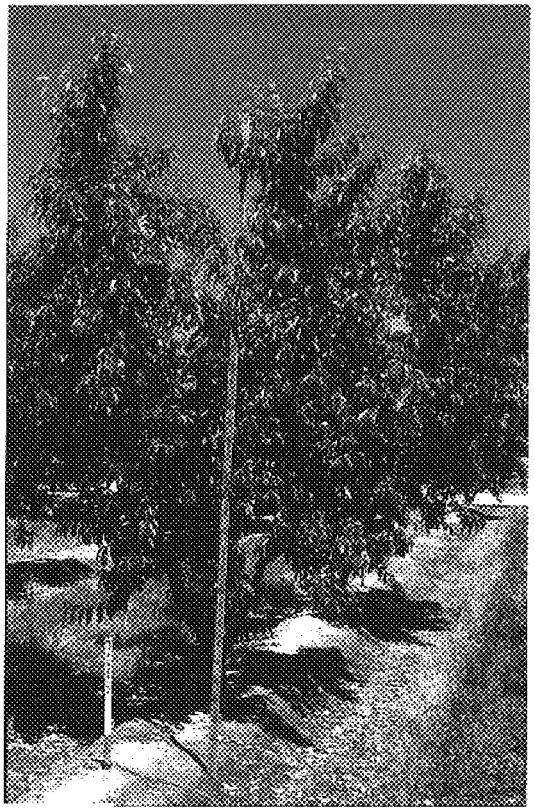
FIG. 9A shows a 'Hiawatha' tree (open pollinated seedling of *P. besseyi*×*P. salicina*)
Figure 9B:
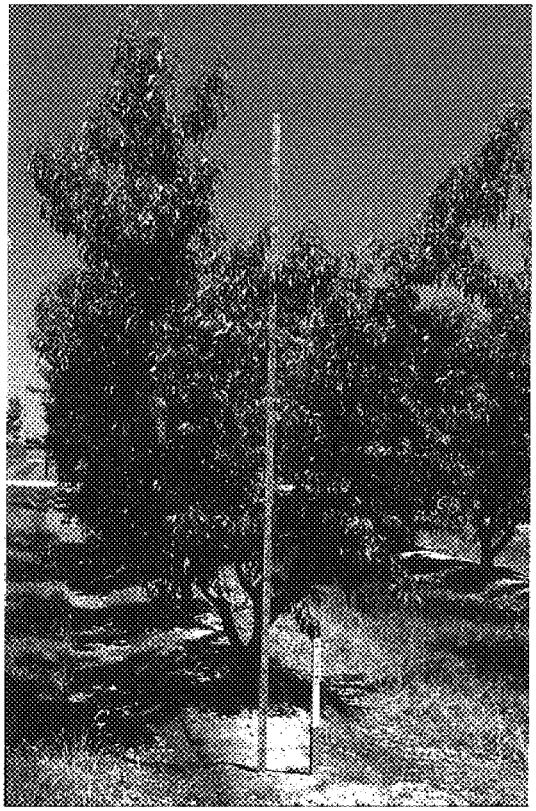
FIG. 9B shows a 'K146-43' plant (*P. salicina* v. *P. Persica*).

Pictures of peach trees on 'Hiawatha' rootstocks (FIG. 9A) and 'K-146-43' (FIG. 9B) illustrate the differences between the two rootstocks.

DISCUSSION

Trunk cross-sectional area: Annual TCA increment and seasonal TCA growth rate. The results of this trial provide a good example of a wide range of vigor induced by peach rootstocks. It has been reported that rootstocks affect not only the absolute growth of the TCA but also the seasonal growth rate pattern of the scion trunk (Bernhard, 1985; Forshey and Elfving, 1989; Swarbrick, 1929; Tustin et al., 1997). Although TCA is not the only parameter used to describe the vegetative growth (Forshey and McKee, 1970; Preston, 1958; Wilcox, 1937a), it is indicative of cumulative growth from planting (Heinicke, 1922; Murray, 1927; Westwood and Roberts, 1970). Based on the initial trunk cross-sectional area (TCA), the six different rootstocks in both the 'Loadel' and the 'Flavorcrest' open vase trees could be grouped in three distinctive categories: I—semi-dwarf or dwarfing rootstocks ('K-146-44' and 'K-146-43'), II—intermediate rootstocks ('Hiawatha,' 'P-30-135' and 'K-119-50'), and III—the most vigorous rootstock ('Nemaguard') which is the control (Table 3).

'Loadel' and 'Flavorcrest' open vase trees grafted on 'K-146-44' and 'K-146-43' grew only 25%–37% as much as trees on 'Nemaguard' (control). In apples, "dwarfing rootstocks", such as 'M9' and 'M27' may produce a tree 15%–35% the size of trees on seedling rootstocks (Rom and Carlson, 1987; Westwood, 1978) so 'K-146-44' and 'K-146-43' rootstocks appear to have effects on peach that are similar to 'M9' and 'M27' on apple.

The yearly TCA increment of both 'Loadel' and 'Flavorcrest' open vase trees followed a pattern similar to the initial TCA except that trees on 'P-30-135', with the 'Flavorcrest' scion, had a high growth rate that was comparable to trees on 'Nemaguard' (Table 3). During 1998, the seasonal TCA growth rate of 'Loadel' and 'Flavorcrest' open vase trees had different patterns depending on the rootstocks (FIG. 5). TCA of trees on the two most dwarfing rootstocks, 'K-146-44' and 'K-146-43', had almost continuous growth during the season, until October, but the TCA increase during August in the other rootstocks declined when the highest seasonal temperatures were recorded. The reduction in TCA growth in the largest rootstocks could have been a consequence of decreased water status after harvest caused by high temperatures, and relatively larger tree canopies, which would have the highest transpiration rate per tree. Canopy size induced by the more vigorous rootstocks also covered the "assigned" surface area more quickly than the smallest rootstocks. This could have reduced the available soil water content for the larger trees more than the smaller trees. Despite the reduction of August TCA growth in trees grafted on the invigorating rootstocks, the daily growth rate throughout the season was lower in trees on 'K-146-44' and 'K-146-43' than in the other rootstocks.

Figure 6:
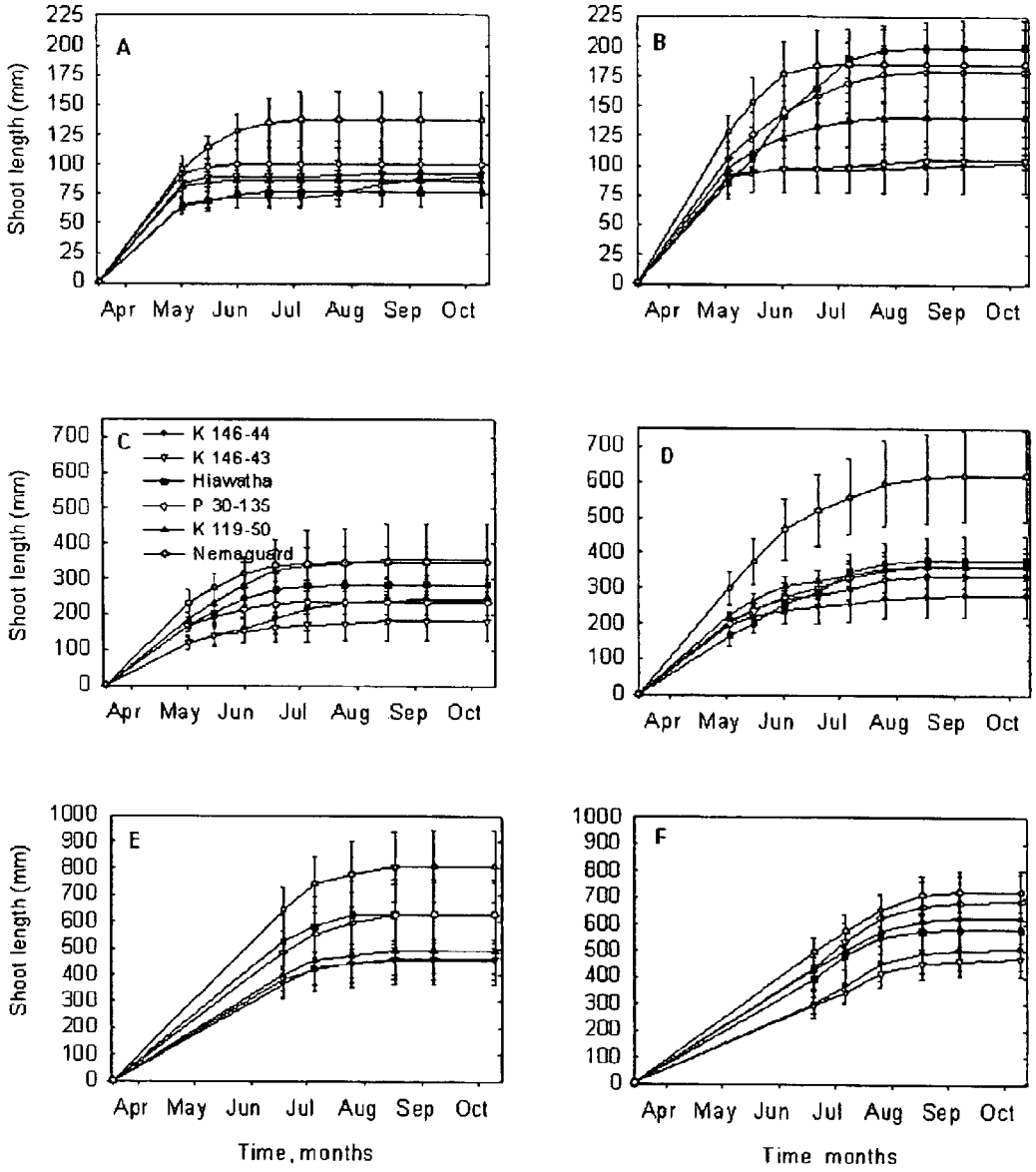
FIG. 6 shows the seasonal pattern of average length of basal stems (B) arising from one-year-old wood (A, B), shoots (S) arising directly from scaffolds (C, D), and terminal shoots (T) arising from one-year-old wood (E, F) in 'Loadel' (A, C, E) and 'Flavorcrest' (B, D, F) open vase trees on six different roostocks. Error bars represent ±1 standard error of the means.

Seasonal shoot growth rate. Several reports indicate that rootstocks markedly affect scion shoot growth and this parameter can be used as an indicator of vigor differences among rootstocks (Barlow, 1964; Forshey and Elfving, 1979; Khatamian and Hilton, 1977). The general growth pattern of shoots in each category (shoot type B, T and S) was similar among the different scion/rootstock combinations with an initial rapid growth and then a slowing growth rate after the middle of the summer. In general, shoots on 'Nemaguard' initially grew faster than on the other rootstocks, while shoots of the trees on 'K-146-44' and 'K-146-43' trees had the lowest growth rates (FIG. 6). More available carbohydrates may have been present in branches, scaffolds, trunk and roots of the large trees at the beginning of the season to allow the faster development of shoots and leaves on the more vigorous rootstocks compared to the dwarf rootstocks. However, no carbohydrates were analyzed in this study. No general differences were noted in the length of the growing season among the different rootstocks. Only 'Hiawatha' appeared to have an earlier slow-down of shoot growth which was accompanied with a decline of TCA increment and earlier leaf fall. Therefore, the observed differences in total shoot length between most rootstocks were attributable to rate of growth rather than length of the shoot growth period. The differences in internode length among the trees on various rootstocks were consistent with this hypothesis.

Figure 7:
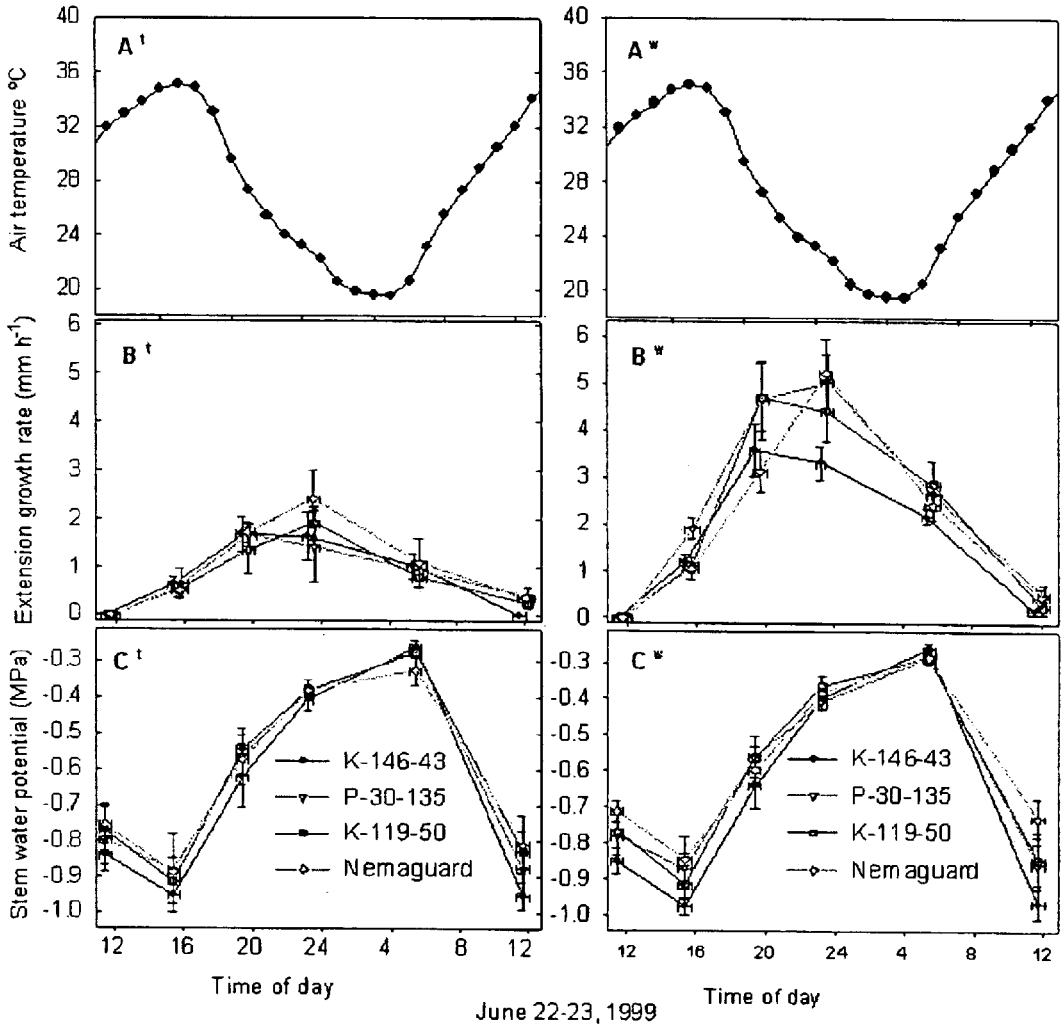
FIG. 7 shows the rootstock influence on the diurnal extension growth rate of terminal shoots (t) and watersprouts (w) of 'Loadel' open vase trees, for Jun. 22–23, 1999. A=Average air temperature; B=hourly stem extension rate; C=diurnal pattern of stem water potential. Vertical error bars represent ±1 standard error of the measurement means and horizontal error bars indicate standard error from the mean time of measurement.

Diurnal extension growth rate affected by rootstocks. Since shoot growth rate must be a function of diurnal shoot growth and Berman and DeJong (1997b) documented that diurnal shoot growth is a function of temperature and changes in stem water potential, we attempted to determine if differences in stem extension growth rate were related to diurnal patterns of stem water potential. The effect of changing water status on plant growth has been demonstrated by many studies (Acevedo et al., 1971; Hsiao and Jing, 1987). Water potential patterns and diurnal shoot growth in the current study were similar to those observed by Simonneau et al (1993) and Berman and DeJong (1997b), with stem dehydration occurring in the morning and rapid hydration occurring in the evening when the transpiration rate decreased. On Jun. 22–23, 1999, trees on 'K-146-43' tended to have lower mean stem water potential and shoot extension growth rate than trees on 'Nemaguard', especially in the afternoon (FIG. 7). In general, trees grafted on dwarfing rootstocks had lower stem water potential which may be related to low stem extension growth during the day. The observed reduction in diurnal stem extension growth rate in the dwarfing rootstocks may indicate the reason for the lower average shoot length of trees grafted on the more size-controlling rootstocks (Table 5). The higher stem water potential found on trees grafted on 'Nemaguard' compared to the more size-controlling ones, in particular 'K-146-43', could be the consequence of differences in hydraulic resistance at the bud union or in the root system (Olien and Lakso, 1984). Further studies related to this particular point could help in the understanding of a diurnal stem extension growth rate mechanism related to dwarfing rootstocks.

Winter measurements: shoots, laterals, watersprout and internode length. It has been reported that rootstocks directly affect the total growth of shoots (Murase et al., 1990; Salvatierra et al., 1998; Stutte et al., 1994; Wilcox, 1937b), and one of the most important parameters is the number and length of shoots and watersprouts because they are related to hand labor activities (pruning, thinning and harvest).

Although only trees on 'Nemaguard' differed significantly from trees on 'K-146-44' in the number of one-year old shoots per tree, there was a tendency for larger trees to have more shoots than smaller trees. The same trend was apparent in the estimated number of lateral shoots per tree, where trees on 'K-146-44' and 'K-146-43' had fewest, while trees on 'Nemaguard' and 'K-119-50' had the most (Table 4). Total shoot length and primary, secondary and tertiary growth per tree were significantly higher in trees grafted on 'Nemaguard' than on 'K-146-44' and 'K-146-43'. Trees on 'K-119-50', 'Hiawatha' and 'P-30-135' had intermediate values (Table 4). Average shoot length also indicated a trend related to tree vigor, where trees on 'Nemaguard' had the longest shoots and trees on the dwarfing rootstocks, 'K-146-44' and 'K-146-43', had the shortest shoots.

Annual TCA increase was related with total shoot growth per tree. Apparently, the total increase in shoot length followed patterns similar to yearly TCA increment (Tables 3 and 4). These results are consistent with reports for apples (Heinicke, 1922; Khatamian and Hilton, 1977; Westwood and Roberts, 1970).

Figure 8:
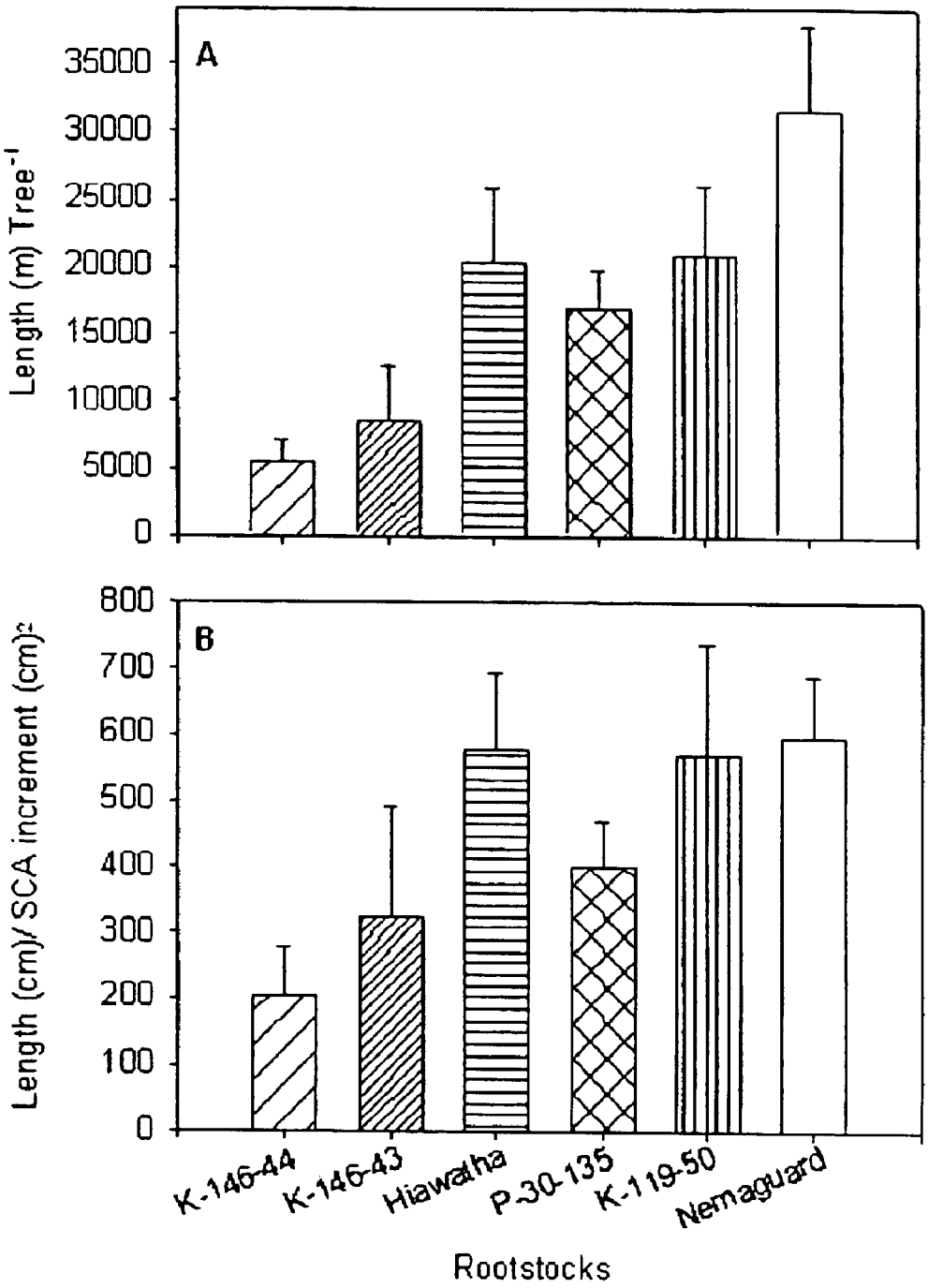
FIG. 8 shows the total length of watersprouts expressed as shoot length (including lateral shoot lengths) per tree (A), and per unit of annual increase of scaffold cross sectional area (B) in 'Loadel' open vase trees on six different rootstocks. Bars indicate ±1 standard error of the mean.

Before initiating the experiment, the presence of the largest shoots, watersprouts, was suspected to be associated with tree vigor. The shoot growth data made it clear that the largest trees, especially trees on 'Nemaguard', had the greatest watersprout growth per tree, including primary, secondary and tertiary growth (FIG. 8). These results suggest that about 50% of the extension growth in the largest trees went into watersprouts, but much of this was removed by summer and dormant pruning (Table 6) representing an inefficiency in the peach production system.

Previous reports have found differences in the insertion angle of shoots induced by apple rootstocks (Crabbé, 1984; Preston, 1968; Warner, 1991). However, there were no significant differences or even trends supporting this concept in this peach experiment (data not shown).

Shoot internode length was associated with tree size. In general, the more size-controlling the rootstock, the shorter the internode length (Table 5). These results agree with Murasse et al. (1990) who reported that peach trees on less vigorous rootstocks produce shorter shoots with shorter internodes. In the present study, trees on more-size controlling rootstocks had shorter internode lengths than trees on the vigorous rootstocks, independent of the size of the shoots.

A noteworthy aspect of the individual shoot growth studies was that the variation in number of nodes of all B shoots arising from the basal nodes of the previous season lateral shoots (hangers) was very low (9.8±0.2). There was slightly more variability in node number of S shoots (laterals shoots arising directly from scaffold wood) (16.3±0.6) and T shoots arising from the terminal vegetative bud on hangers (31.9±0.6). The consistent number of nodes of B shoots may reflect the number of "preformed" nodes inherent in lateral vegetative buds in this position on shoots of this cultivar ('Loadel'). If this is the case it would indicate that shoot growth in specific locations in peach trees is more determinate than commonly thought (Kramer and Kozlowski, 1979). The fact that the three different types of shoots had three different but relatively consistent node numbers per shoot may indicate that individual shoot node number is more dependent on point of morphological origin on the tree than the environmental condition/exposure during growth (Sabatier and Barthelemy, 2001).

Influence of rootstocks on summer and winter pruning. Previous studies have indicated that pruning (summer and winter) is correlated with the size of the trees and particularly with rootstock vigor (Barlow, 1964, 1971; Forshey and McKee, 1970). Required summer and winter pruning was directly associated with the size of trees. It was necessary to remove more material from trees on 'Nemaguard', especially watersprouts. Dry weight removed from summer pruning of 'Loadel' and 'Flavorcrest' open vase trees on 'K-146-44' was approximately 3% and 14%, respectively, of trees on 'Nemaguard' (Table 6). Dormant pruning dry weight differences were similar. It is clear that dwarf peach rootstocks have advantages over more invigorating rootstocks relative to reduced summer and dormant pruning, and it is encouraging that major differences in vegetative growth between these roostocks may be classified as "excessive" since much of it is growth that is removed during commercial pruning procedures.

Influence of rootstocks on tree yield. The fruit yield responses in this study are comparable to other research on peach rootstocks (Felipe et al., 1997; Minguzzi and Poli, 1988; Murase et al., 1990) where the general trend of the larger the tree the higher the yield per tree appears to fit. In California, 'Nemaguard' rootstock is known for producing trees with high vigor and high yields of large fruit. Clearly, the size-controlling rootstocks in this study produced trees with less vigor but unfortunately also less yield. However, since the trees in this study were only in their third year in the orchard it is too early to draw too many conclusions about the ultimate production efficiency of the various rootstocks. Longer-term yield data have been collected and reported elsewhere (DeJong et al., 2003).

The differences in tree yield and crop load between the 'Loadel' and 'Flavorcrest' scion cultivars on the various rootstocks may account for the tendency toward the apparent greater vigor of the 'Flavorcrest' trees compared to the 'Loadel' trees in some of the vegetative growth measurements. However, clearly most of the differences in vegetative growth among rootstock with the same scion cultivar are due to rootstock differences and not crop load since crop load and yield were least on tree of the smaller rootstocks.

This experiment demonstrated significant effects of the tested rootstocks on vegetative growth of two peach cultivars. Annual TCA increment was related to the annual shoot growth in all the rootstocks. No marked differences were found in the general seasonal pattern of shoot growth among the studied rootstocks, but trees on the more vigorous rootstocks initially grew more rapidly than trees on the smallest rootstocks. Variations in shoot growth length were attributed to variations in the daily extension shoot growth, where the invigorating rootstocks induced the scion to grow faster than trees on the more size-controlling rootstocks. Correspondingly, average shoot and internode lengths were reduced in trees on the more size-controlling rootstocks. No differences were found in the insertion angle of shoots among trees on all the rootstocks. Total shoot growth per tree was proportional to the induced size, where watersprouts contributed to half of the growth with the vigorous rootstocks and only one-third to one-fourth of the growth on dwarfing rootstocks. However, shoot growth per unit of scaffold cross-sectional area was comparable among all but the smallest rootstocks. Summer and winter pruning was related to tree size so that trees grafted on the more size-controlling rootstocks, 'K-146-44' and 'K-146-43', required the least pruning.

LITERATURE CITED FOR COMPARISON #2

Acevedo, E, T. C. Hsiao, and D. W. Henderson. 1971. Immediate and subsequent growth responses of maize leaves to changes in water status. Plant Physiol. 48:631–636.

Barlow, H. W. 1964. An interim report on a long-term experiment to assess the effect of cropping on apple tree growth. Annu. Rpt. E. Malling Res. Sta. 1963:84–93.

Barlow, H. W. 1971. Plant physiology. Annu. Rpt. E. Malling Res. Sta. 1971: 55–67.

Berman, M. E. and T. M. DeJong. 1996. Water stress and crop load effects on fruit fresh and dry weights in peach (*Prunus persica*). Tree Physiol. 16:859–864.

Berman, M. E. and T. M. DeJong. 1997a. Crop load and water stress effects on daily stem growth in peach (*Prunus persica*). Tree Physiol. 17:467–472.

Berman, M. E. and T. M. DeJong. 1997b. Diurnal patterns of stem extension growth in peach (*Prunus persica*): temperature and fluctuations in water status determine growth rate. Physiol. Plant. 100:361–370.

Bernhard, R. 1985. Rootstock influence on the growing rhythm and on the fertility of peach trees. Acta Hort. 173:191–197.

Chalmers, D. J. and I. B. Wilson. 1978. Productivity of peach trees: Tree growth and water stress in relation to fruit growth and assimilate demand. Ann. Bot. 42:294–295.

Childers, N. F. 1983. Modern fruit science. Orchard and small fruit cultures. 9th ed. Gainesville, Fla. Hort. Pub. p. 583.

Crabbé, J. J. 1984. Morphogenetical ways towards vigor restriction in spontaneous and man-made dwarf trees. Acta Hort. 146:113–117.

DeJong, T. M., J. F. Doyle, and K. R. Day. 1987. Seasonal patterns of reproductive and vegetative sink activity in early and late maturing peach (*Prunus persica*) cultivars. Physiol. Plant. 71:83–88.

DeJong, T. M., J. F. Doyle, R. S. Johnson, and D. Ramming. 1997. Evaluation of size controlling rootstocks for California peach production. Annu. Res. Rpt. Calif. Tree Fruit Agreement, Reedley, Calif.

DeJong, T. M., R. S. Johnson, J. F. Doyle, A. Weibel, L. Solari, B. Basile, J. Marsal, D. Ramming, and D. Bryla. 2003. Growth yield and physiological behavior of size-controling peach rootstocks developed in California. Acta Hort. (in press)

DeJong, T. M., W. Tsuji, J. F. Doyle, and Y. L. Grossman. 1999. Comparative economic efficiency of four peach production systems in California. HortScience 34:73–78.

Felipe, A., M. Carrera, and J. Gomez-Aparisi. 1997. 'Montizo' and 'Monpol', two new plum rootstocks for peaches. Acta Hort. 451:273–276.

Forshey, C. G. and D. C. Elfving. 1979. Estimating yield and fruit numbers of apple trees from branch samples. J. Amer. Soc. Hort. Sci. 104:897–900.

Forshey, C. G. and D. C. Elfving. 1989. The relationship between vegetative growth and fruiting in apple trees. Hort. Rev. 11:229–287.

Forshey, C. G. and W. M. W. McKee. 1970. Production efficiency of a large and small "McIntosh" apple tree. HortScience 5:164–165.

Glenn, D. M. and R. Scorza. 1992. Reciprocal grafts of standard and dwarf peach alter dry-matter partitioning and root physiology. HortScience 27:241–243.

Heinicke, A. J. 1922. Some relationship between the circumference and weight, and between root top growth of young apple trees. Proc. Amer. Soc. Hort. Sci. 18:222–227.

Hsiao, T. C. and J. Jing. 1987. Leaf and root expansive growth in response to water deficits. Physiology of cell expansion during plant growth. Proc. Second Annu. Penn State Symp. Plant Physiol. 180–192.

Jones, O. P. 1984. Mode of action of rootstock/scion interactions in apple and cherry trees. Acta Hort. 146:175–182.

Kamboj, J. S., P. S. Blake, J. D. Quinlan, and A. D. Webster. 1997. Recent advances in studies on the dwarfing mechanism of apple roostocks. Acta Hort. 451:75–82.

Khatamian, H. and R. J. Hilton. 1977. The relationship between shoot growth and area of trunk cross-section in several woody plant species. HortScience 12:255–257.

Kramer, P. J. and T. T. Kozlowski. 1979. Physiology of Woody Plants. Academic Press, New York.

Larson, K. D., T. M. DeJong, and R. S. Johnson. 1988. Physiological and growth responses of mature peach trees to postharvest water stress. J. Amer. Soc. Hort. Sci. 113:296–300.

Lockard, R. G., G. W. Schneider, and T. R. Kemp. 1982. Phenolic compounds in two size-controlling apple rootstocks. J. Amer. Soc. Hort. Sci. 107:183–186.

Maggs, D. H. 1957. A comparison for the growth patterns of two apple rootstock varieties during their first year. Annu. Rpt. E. Malling. Res. Sta. 101–105.

McCutchan H. and K. A. Shackel. 1992. Stem-water potential as a sensitive indicator of water stress in prune trees (*Prunus domestica* L. Cv French). J. Amer. Soc. Hort. Sci. 117:607–611.

McKenzie, D. W. 1961. Rootstock-scion interaction in apples, with special reference to root anatomy, J. Hort. Sci. 36:40–47.

Minguzzi, A. and M. Poli. 1988. Influenza del portinnesto nel reimpianto del pesco. L'Informatore Agrario 32:77–79.

Murase, S., T. Yamazaki, Y. Inomata, and K. Suzuki. 1990. Dwarfing rootstock for peach. Japan Agr. Res. Quart. 23:294–300.

Murray, C. D. 1927. A relationship between circumference and weight in trees and its bearing on branching angles. J. Gen. Physiol. 10:725–729.

Olien, W. C. and A. N. Lakso. 1984. A comparison of the dwarf character and water relations of five apple rootstocks. Acta Hort. 146:151–158.

Preston, A. P. 1958. Apple rootstock studies. Thirty-five years' results with Lane's Prince Albert on clonal rootstock. J. Hort. Sci. 33:29–38.

Preston, A. P. 1968. Pruning and rootstock as factors in the production of primary branches on apple trees. J. Hort. Sci. 48:17–22.

Richards, D., W. K. Thompson, and R. P. Pharis. 1986. The influence of dwarfing interstocks on the distribution and metabolism of xylem-applied [$^3$H] Giberellin A4 in apple. Plant Physiol. 82:1090–1095.

Rom, R. C. and R. F. Carlson. 1987. Roostocks for fruit crops. Wiley, New York.

Sabatier, S. and D. Barthelemy. 2001. Bud structure in relation to shoot morphology and position on the vegetative annual shoots of *Juglans regia* L. (*Juglandaceae*). Ann. Bot. 87:117–123.

Salvatierra, M. A., H. Gemma, and S. Iwahori. 1998. Partitioning of carbohydrates and development of tissues in the graft union of peaches grafted on *Prunus tomentosa* Thunb. rootstock. J. Japan Soc. Hort. Sci. 67:475–482.

Simonneau, T., R. Habib, J. P., Goutouly, and J. G. Huguet. 1993a. Diurnal changes in stem diameter depend upon variation in water content: direct evidence in peach trees. J. Exp. Bot. 44:615–621.

Simonneau, T., R. Habib, and A. Leconte. 1993b. Diurnal changes in stem diameter and plant water content in peach trees. Acta Hort. 335:191–159.

Simons, R. K. and M. C. Chu. 1984. Tissue development within the graft union as related to dwarfing in apple. Acta Hort. 146:203–210.

Soumelidou, K., N. H. Battey, P. Jhon, and J. R. Barnett. 1994. The anatomy of the developing bud union and its relationship to dwarfing in apple. Ann. of Bot. 74:605–611.

Stutte, G. W., T. A. Baugher, S. P. Walter, D. W. Leach, D. M. Glenn, and T. J. Tworkoski. 1994. Rootstock and training system affect dry-matter and carbohydrate distribution in 'Golden Delicious' apple trees. J. Amer. Soc. Hort. Sci. 119:492–497.

Swarbrick, T. 1929. Factors governing fruit bud formation. VIII. The seasonal elongation growth of apple varieties on some vegetative rootstocks; and its possible relation to fruit bud formation. J. Pomol. 7:100–129.

Tustin, S., D. Ferree, S. Myers, L. Corelli-Grappadelli, A. Lakso, T. Robinson, J. Flore, R. Perry, S. Breitkreutz, B. Barritt, B. Konishi, C. Rom, L. Taylor, A. Webster, C. Atkinson, J. Palmer, and W. Cashmore. 1997. The international apple growth study. Acta Hort. 451:693–699.

Ussahatanonta, S. and R. K. Simons. 1988. Graft union development of the 'Golden Delicious' apple when combined with varied dwarfing rootstocks. Fruit Var. J. 42:152–159.

Vyvyan, M. C. 1935. Leaf relations of fruit trees. II. The census method for recording summer growth, with special reference to the apple. J. Pom. Hort. Sci. 13:209–219.

Warner, J. 1991. Rootstock affects primary scaffold branch crotch angle of apple trees. HortScience 26:1266–1267.

Webster, A. D. 2001. Rootstocks for temperate fruit crops: current uses, future potential and alternative strategies. Acta Hort. 557:25–34.

Westwood, M. N. 1978. Temperate-Zone Pomology. Freeman. San Francisco. pp.88–107.

Westwood, M. N. and A. N. Roberts. 1970. The relationship between trunk cross-sectional area and weight of apple trees. J. Amer. Soc. Hort. Sci. 95:28–30.

Wilcox, J. C. 1937a. Field studies of apple tree growth and fruiting. III. Some observations on the measurement of tree vigor. Sci. Agr. 17:657–669.

Wilcox, J. C. 1937b. Field studies of apple tree growth and fruiting. II. Correlations between growth and fruiting. Sci. Agr. 17:573–586.

Zimmermann M. H. 1983. Xylem Structure and the Ascent of Sap. Springler-Verlag, Berlin.

TABLE 1

Trunk circumferences (cm) of Flavorcrest and Loadel scion cultivars on six rootstocks and two training systems at the end of the sixth growing season (December 2001). Values represent the mean (∀ SE) of measurements of the four replications in the high density 'KAC-V' and standard density "open vase" parts of the trial.

| | LOADEL | | FLAVORCREST | |
|---|---|---|---|---|
| ROOTSTOCK | Open Vase | KAC-V | Open Vase | KAC-V |
| Nemaguard | 56 ± 0.5 | 39 ± 0.7 | 65 ± 1.0 | 46 ± 1.1 |
| K-119-50 | 48 ± 0.8 | 33 ± 1.8 | 54 ± 2.1 | 38 ± 1.5 |
| P-30-135 | 52 ± 1.5 | 36 ± 2.2 | 62 ± 1.5 | 43 ± 3.1 |
| Hiawatha | 46 ± 0.9 | 34 ± 1.2 | 50 ± 2.0 | 37 ± 2.0 |
| K-146-43 | 36 ± 0.5 | 27 ± 0.7 | 42 ± 0.3 | 27 ± 0.7 |
| K-146-44 | 35 ± 1.7 | 28 ± 0.5 | 42 ± 0.6 | 28 ± 0.6 |

TABLE 2

Calculated mean modified harvest increments (kg fruit dry weight/kg pruning weight) of years three through six for two peach scion cultivars (Loadel and Flavorcrest) in two training systems (KAC-V and Open Vase) on six root stocks.

| | Year 3 | Year 4 | Year 5 | Year 6 |
|---|---|---|---|---|
| Loadel, KAC-V | | | | |
| Nemaguard | 0.62 | 1.62 | 0.92 | 0.72 |
| K-119-50 | 0.72 | 2.26 | 1.09 | 1.07 |

TABLE 2-continued

Calculated mean modified harvest increments (kg fruit dry weight/kg pruning weight) of years three through six for two peach scion cultivars (Loadel and Flavorcrest) in two training systems (KAC-V and Open Vase) on six root stocks.

| | Year 3 | Year 4 | Year 5 | Year 6 |
|---|---|---|---|---|
| P-30-135 | 0.95 | 2.55 | 1.27 | 1.05 |
| Hiawatha | 0.81 | 2.29 | 0.70 | 1.21 |
| K-146-43 | 1.07 | 4.36 | 1.75 | 2.12 |
| K-146-44 | 1.26 | 4.12 | 1.59 | 1.79 |
| Flavorcrest, KAC-V | | | | |
| Nemaguard | 0.20 | 0.47 | 0.66 | 0.42 |
| K-119-50 | 0.30 | 0.94 | 1.13 | 0.56 |
| P-30-135 | 0.23 | 0.79 | 1.00 | 0.51 |
| Hiawatha | 0.24 | 0.76 | 1.06 | 0.60 |
| K-146-43 | 0.74 | 1.53 | 2.14 | 0.76 |
| K-146-44 | 0.50 | 1.26 | 1.74 | 0.97 |
| Loadel, Open Vase | | | | |
| Nemaguard | 0.85 | 2.10 | 1.32 | 1.31 |
| K-119-50 | 1.19 | 3.43 | 1.81 | 2.08 |
| P-30-135 | 1.25 | 2.91 | 1.81 | 1.75 |
| Hiawatha | 1.57 | 3.47 | 2.00 | 2.09 |
| K-146-43 | 1.85 | 4.46 | 1.79 | 3.21 |
| K-146-44 | 3.13 | 4.41 | — | 3.08 |
| Flavorcrest, Open Vase | | | | |
| Nemaguard | 0.33 | 0.80 | 1.06 | 0.61 |
| K-119-50 | 0.36 | 1.18 | 1.30 | 0.88 |
| P-30-135 | 0.32 | 1.01 | 1.10 | 0.81 |
| Hiawatha | 0.44 | 1.59 | 1.23 | 1.09 |
| K-146-43 | 0.57 | 1.79 | 1.88 | 1.68 |
| K-146-44 | 0.62 | 1.38 | 1.34 | 1.42 |

TABLE 3

Mean annual TCA increment of three-year-old 'Loadel' and 'Flavorcrest' open vase trees grafted on six different rootstocks.

| | Loadel | |
|---|---|---|
| ROOTSTOCK | Initial TCA ($cm^2$) | Yearly TCA increment ($cm^2$) |
| K-146-44 | 18.6 (1.91) c[z] | 14.7 (2.22) c |
| K-146-43 | 25.6 (2.03) c | 17.6 (1.81) c |
| Hiawatha | 54.6 (3.35) b | 37.2 (2.44) b |
| P-30-135 | 59.6 (2.69) b | 37.5 (1.93) b |
| K-119-50 | 56.3 (1.77) b | 36.9 (2.00) b |
| Nemaguard | 74.0 (2.66) a | 57.2 (2.05) a |
| | Flavorcrest | |
| ROOTSTOCK | Initial TCA ($cm^2$) | Yearly TCA increment ($cm^2$) |
| K-146-44 | 24.3 (0.89) c | 27.4 (0.77) b |
| K-146-43 | 28.4 (2.24) c | 29.0 (2.01) b |
| Hiawatha | 52.4 (5.97) b | 47.7 (4.40) c |
| P-30-135 | 57.6 (2.31) b | 70.0 (1.94) a |
| K-119-50 | 51.8 (6.05) b | 54.0 (2.52) b |
| Nemaguard | 77.4 (2.14) a | 75.0 (2.83) a |

[z]Different letters within columns indicate that means differ significantly (Tukey $P < 0.05$). Numbers in parenthesis are SE.

TABLE 4

Calculated mean number of one-year old shoots, new lateral shoots and growth in length per tree in 'Loadel' open vase trees, on six different rootstocks.

| Rootstocks | Number of one year old shoots/tree[z,y] | Number of new lateral shoots/tree[x] |
|---|---|---|
| K-146-44 | 628.0 (88.1) b | 142.0 (34.6) b |
| K-146-43 | 809.0 (125) ab | 202.3 (47.1) b |
| Hiawatha | 985.5 (107) ab | 603.3 (58.1) ab |
| P-30-135 | 922.4 (117) ab | 429.7 (60.4) ab |
| K-119-50 | 1,022.1 (108) ab | 599.7 (88.3) a |
| Nemaguard | 1,266.4 (78.5) a | 888.7 (253) a |

| | Shoot length per tree | | |
|---|---|---|---|
| Rootstocks | Primary growth/tree (m)[w] | Secondary and tertiary growth/tree (m)[v] | Total growth/tree (m)[u] |
| K-146-44 | 122.39 (19.75) d | 37.46 (9.85) c | 159.85 (23.94) c |
| K-146-43 | 152.31 (8.29) cd | 51.22 (15.69) bc | 203.53 (14.48) c |
| Hiawatha | 238.73 (19.74) b | 177.11 (22.02) a | 415.83 (24.18) b |
| P-30-135 | 215.48 (18.39) bc | 155.73 (22.75) ab | 354.99 (35.83) b |
| K-119-50 | 247.41 (17.63) b | 184.66 (22.20) a | 432.07 (33.67) b |
| Nemaguard | 366.08 (24.12) a | 231.42 (38.72) a | 597.50 (60.89) a |

[z]Different letters within columns indicate that means differ significantly (Tukey $P < 0.05$). Numbers in parenthesis are SE.
[y]One year old shoots.
[x]Total number of laterals includes laterals of second and third order growth.
[w]Growth originated by a dormant bud.
[v]Growth originated from lateral and sublateral buds during the vegetative growth period.
[u]Primary, secondary and tertiary growth added.

Proposed Field Test of the Lins Method Thermal Oil Recovery Process in Athabasca McMurray Tar Sands, Husky Oil Company.

What is claimed is:

1. A new and distinct peach and nectarine rootstock plant, 'K146-43', as herein described and illustrated.

* * * * *